United States Patent [19]
Willey

[11] Patent Number: 5,679,661
[45] Date of Patent: Oct. 21, 1997

[54] LOW HUE PHOTODISINFECTANTS

[75] Inventor: Alan David Willey, Cincinnati, Ohio

[73] Assignee: The Procter & Gamble Company, Cincinnati, Ohio

[21] Appl. No.: 659,652

[22] Filed: Jun. 18, 1996

Related U.S. Application Data

[63] Continuation-in-part of Ser. No. 506,652, Jul. 25, 1995, abandoned.

[51] Int. Cl.$^6$ .................................................. A01N 55/00
[52] U.S. Cl. ........................................................ 514/63
[58] Field of Search ............................................ 514/63

[56] References Cited

U.S. PATENT DOCUMENTS

| | | | |
|---|---|---|---|
| 3,094,536 | 6/1963 | Kenney et al. | 260/314.5 |
| 3,927,967 | 12/1975 | Speakman | 8/103 |
| 4,033,718 | 7/1977 | Holocombe et al. | 8/103 |
| 4,166,718 | 9/1979 | Reinert et al. | 8/111 |
| 4,240,920 | 12/1980 | de Luque | 252/99 |
| 4,255,273 | 3/1981 | Sakkab | 252/102 |
| 4,256,597 | 3/1981 | Sakkab | 252/99 |
| 4,318,883 | 3/1982 | Polony et al. | 422/22 |
| 4,368,053 | 1/1983 | Eckhardt et al. | 8/102 |
| 4,456,452 | 6/1984 | Holzle et al. | 8/103 |
| 4,497,741 | 2/1985 | Holzle et al. | 260/245.77 |
| 4,648,992 | 3/1987 | Graf et al. | 540/124 |
| 4,657,554 | 4/1987 | Reinert et al. | 8/107 |
| 5,403,928 | 4/1995 | Arrhenuis | 540/128 |
| 5,486,274 | 1/1996 | Thetford et al. | 204/157.5 |

FOREIGN PATENT DOCUMENTS

| | | | |
|---|---|---|---|
| 0 484 027 A1 | 5/1992 | European Pat. Off. | C09B 47/04 |
| 6-73397 | 3/1994 | Japan | C11D 3/395 |
| 1372035 | 10/1974 | United Kingdom | D06L 3/04 |
| 1408144 | 10/1975 | United Kingdom | D06L 3/04 |
| WO 91/18007 | 11/1991 | WIPO | C07J 43/00 |

OTHER PUBLICATIONS

Cook et al., "Octa-alkoxy Phthalocyanine and Naphthalocyanine Derivatives: Dyes with Q–Band Absorption in the Far Red or Near Infrared", J. Chem. Soc. Perkin Trans. (Jan. 18, 1988) pp. 2453–2458.

Esposito et al., "The Synthesis and Physical Properties of Some Organo–and Organosiloxysilicon Phthalocyanines", Organo–and Organosiloxysilicon Phthalocyanines, vol. 5, No. 11 (Nov., 1986) p. 1979.

Ford et al., "Synthesis and Photochemical Properties of Aluminum, Gallium, Silicon, and Tin Naphthalocyamines", Inorg. Chem., vol. 31 (Mar. 5, 1992), pp. 3371–3377.

Joyner et al., "Phthalocyaninosilicon Compounds", Inorganic Chemistry (Sep. 14, 1961), pp. 236–238.

Kroenke et al., "The Infrared Spectra of Some Tin and Lead Phthalocyanines", Inorganic Chemistry (Aug. 29, 1983), pp. 696–698.

Lowery et al., "Dichloro(phthalocyanino)silicon", Inorganic Chemistry (Aug. 17, 1964), p. 128.

Wheeler et al., "A Silicon Phthalocyanine and a Silicon Naphthalocyanine: Synthesis, Electrochemistry, and Electrogenerated Chemiluminescence", J. Am. Chem. Soc., vol. 106 (Feb. 21, 1984), p. 7404.

Witkiewicz et al., "Properties of octamethoxyphthalocyanines, I. On their syntheses, electrical conductivity, and catalytic activity", Materials Science II/1-2 (1976); pp. 39–45.

Stillman et al., "Absorption and Magnetic Circular Dichroism Spectral Properties of Phthalocyanines, Part 1: Complexes of the Dianion, Pc(-2)", pp. 135–289.

*Primary Examiner*—Melvyn I. Marquis
*Attorney, Agent, or Firm*—Richard S. Echler, Sr.; Kim William Zerby; Jacobus C. Rasser

[57] ABSTRACT

Low hue photo disinfecting compositions comprising organosilicon(IV) phthalocyanine and naphthalocyanines having Q-band absorption maxima at wavelengths greater than 660 nm and increased triplet state yields whereby production of singlet oxygen is increased.

36 Claims, No Drawings

LOW HUE PHOTODISINFECTANTS

This application is a Continuation-In-Part of patent application U.S. Ser. No. 08/505,652, filed Jul. 25, 1995, abandoned.

FIELD OF THE INVENTION

The present invention relates to novel organosilicon photosensitizing compounds having a Q-band maximum absorption wavelength of 660 nanometers or greater and their use as photoactivators (photosensitizer) or singlet oxygen producers, in particular for low hue photodisinfecting of textiles, paper-based textile articles, aseptic barriers and hard surfaces. The present invention further relates to methods for treating swimming pools and baths. The present invention further relates to a method of treating non-potable water and for treating sewage effluent.

BACKGROUND OF THE INVENTION

It is known that various water-soluble phthalocyanine and naphthalocyanine compounds, in particular those having certain metals as the central atom, have a photosensitizing action and can therefore be used as photodisinfectant agents or anti-microbial active compounds.

Phthalocyanines and naphthalocyanines especially when combined with a suitable metal can undergo a series of photochemical reactions in conjunction with molecular oxygen to produce molecules of "singlet oxygen". The excited "singlet oxygen", formed in these photosensitizing reactions, is an oxidative species capable of reacting with stains to chemically bleach them to a colorless and usually water-soluble state, thereby resulting in what is called photochemical bleaching.

There are many examples of photodisinfectants comprising phthalocyanines and naphthalocyanines that use this photobleaching principle as a means to achieve disinfecting properties, the most common being the zinc and aluminum phthalocyanines. In the literature the term "photosensitizer" is often used instead of "photoactivator" and may therefore be considered as standing equally well for the latter term used throughout this specification. The term "photodisinfectant" will stand for the term "photo anti-microbial" or "photosanitizer" and stand equally well for the latter terms used throughout this specification.

The prior art teaches phthalocyanine and naphthalocyanine compounds having the general structure

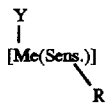

where Me is a transition or non-transition metal, (Sens.) is a phthalocyanine or naphthalocyanine ring which, when combined with a suitable Me unit, is capable of undergoing photosensitization of oxygen molecules, R units are substituent groups which are bonded to the photosensitization ring units (Sens.) to enhance the solubility or photochemical properties of the molecule, and Y units are substituents associated with the metal atom, for example, anions to provide electronic neutrality. The selection of a particular substituent R unit for substitution into the molecule has been the focus of many years of research and these units are typically chosen by the formulator to impart into the target molecule the desired level of water solubility without affecting the degree of photosensitizing properties.

A major limitation to the use of phthalocyanine and naphthalocyanine compounds for fabric photodisinfecting is the fact that these molecules have a Q-band absorption maxima ($\lambda_{max}$) in the range of visible light. Therefore, they are highly colored materials. Phthalocyanines have Q-band absorption in the range of 600–700 nanometers, while naphthalocyanines have Q-band absorption in the 700–800 nanometer range. This is not surprising given the fact that these molecules are structurally similar to dyestuffs.

A second limitation arises from the fact that the parent phthalocyanine and naphthalocyanine compounds when combined with a transition or non-transition metal are not inherently water soluble. This fact is especially true in the case of naphthalocyanines. It has therefore been the task of phthalocyanine and naphthalocyanine photodisinfectant formulators to select for R units moieties that are polar or hydrophilic, then attach these moieties to the (Sens.) unit in an attempt to increase the molecule's water solubility without adversely affecting the photochemical properties of the ring system.

A further task for the formulators of phthalocyanines and naphthalocyanines has been the need to modify the properties of the (Sens.) unit of the molecule to increase the "photodisinfecting capacity" (photophysics) of the molecule, in other words, to increase the quantum efficiency. Again, selection of suitable R units to accomplish this task must not in turn adversely affect the water solubility. While balancing water solubility and enhanced photophysics, the formulator must insure that the structural modifications do no shift the $\lambda_{max}$ of the Q-band to a wavelength that is now in the visible region. When the Q-band $\lambda_{max}$ is a wavelength from 660 nm to about 700 nm, while not having the more desirable "low hue" properties of materials exhibiting a Q-band $\lambda_{max}$ of 700 nm or greater, it still provides a molecule with photodisinfecting properties acceptable to consumers. These "colored" materials have wide utility in treating swimming pools and sewage effluents since the presence of color can indicate the presence of active disinfectant.

It is well known to formulators skilled in the art that an R unit which may produce a desired increase in one of these three properties may cause an equally large decrease in one or all of the other desirable properties. For example, a change which increases solubility may reduce the quantum efficiency of the molecule and thereby render the final molecule without sufficient photodisinfecting properties. Exacerbating this problem further is another factor; choice of a suitable Y group. Many phthalocyanine and naphthalocyanines comprise a metal or non-metal atom that is hypervalent to the chelate ring system. Satisfying the valency requirement of these atoms or providing for the electronic neutrality of the molecule may cause the delicate balance of properties, once achieved, to collapse.

Surprisingly, it has been found that the compounds of the present invention allow the formulators to modify the levels of solubility, photoefficiency, Q-band wavelength maxima and the electronic requirements of the central silicon atom separately without adversely affecting the other parameters of the molecule. This ability to delineate and selectively modify the key structural elements contributing to the target properties of the molecule allows the formulator to proceed without having to rely upon a "hit and miss" stratagem.

One key to this ability to control the molecular properties is found when contrasting the structure of known photodisinfectants comprising phthalocyanines and naphthalocyanines with those of the present invention. The examples of photodisinfectants or photo anti-microbial materials previously described in the art are generally flat molecules due to their planar ring structure. This inherently leads to molecular stacking, layering and other forms of aggregation which tend to clump the molecules together. A photodisinfectant molecule which is overlaid by other photodisinfectant molecules will tend to quench one another thereby effectively stopping the generation of singlet oxygen.

The organosilicon photosensitizing compounds of the present invention comprise axial substituents that act to break up this ordering effect, hence providing an efficiently formed mono-layer of photosensitizers evenly applied to a given substrate. Because each molecule of this mono-layer can now contribute to disinfecting, there is better cost efficiency to the formulator.

It has been surprisingly found that because of the separating of physical properties into "molecular sectors", e.g. R groups for solubility, new uses for the compounds of the present invention have been realized. Adducts which provide unique solubility profiles, but which detract from the photophysics, were once excluded from use in photodisinfectants. However, the inclusion of these moieties into the photodisinfectants of the present invention results in the ability to formulate photodisinfectants for use with non-classical carriers. Solvent based or low aqueous solutions of the present invention are now obtainable for the very reason that control over solubility is manifest in the choice of the axial R substitutions.

The proper selection of axial R units attached to the compounds of the present invention allow the formulator to balance the changes in photoefficiency of the desired compound with the water solubility of the parent material. In addition, these axial R unit modifications provide the formulator with the ability to balance solubility, Q-band $\lambda_{max}$ and quantum efficiency of the (Sens.) unit.

It is an object of the present invention to provide "substantive" and "non-substantive" organosilicon photosensitizers. The terms "substantive" and "non-substantive", as used in the present specification and as further defined hereinafter, describe the propensity of a compound to elicit a surface affinity or, in the alternative, the lack of a surface affinity, in other words a "substantive" organosilicon photosensitizer will be attracted to a surface while a "non-substantive" organosilicon photosensitizer will repel a surface.

It is a further object of the present invention to provide a method for treating disposable articles of manufacture comprising paper or textiles with substantive and non-substantive photodisinfectanting compositions.

It is a further object of the present invention to provide a method for photo disinfecting surfaces by applying compositions comprising substantive photo disinfecting compositions to non-porous hard surfaces, inter alia, Formic®, ceramic tile, glass, or for porous hard surfaces such as concrete or wood.

An object of the present invention is to provide a method for disinfecting swimming pools and baths.

An object of the present invention is to provide photo-disinfectants that can be used in solvent based applications or in low aqueous solutions, that is where water makes up for less than half of the carrier liquid.

It is a further object of the present invention to provide a method for making water potable for human usage and a method for maintaining water potable.

Also an object of the present invention is to prevent exposure of humans to micro organisms by treating a situs or an article of manufacture with a photo-disinfecting compound.

An object of the present invention is to provide for low hue organosilicon photosensitizing compounds with photo disinfecting properties having a Q-band maximum absorption wavelength of at least 660 nanometers.

BACKGROUND ART

Various patent documents relate to photochemical bleaching or to the use of phthalocyanine and naphthalocyanine compounds as well as their formulation and synthesis. See for example U.S. Pat. No. 3,094,536 issued Jun. 18, 1963; U.S. Pat. No. 3,927,967 issued Dec. 23, 1975; U.S. Pat. No. 4,033,718 issued Jul. 5, 1977; U.S. Pat. No. 4,166,718 issued Sep. 4, 1979; U.S. Pat. No. 4,240,920 issued Dec. 23, 1980; U.S. Pat. No. 4,255,273 issued Mar. 10, 1981; U.S. Pat. No. 4,256,597 issued Mar. 17, 1981; U.S. Pat. No. 4,318,883 issued Mar. 9, 1982; U.S. Pat. No. 4,368,053 issued Jan. 11, 1983; U.S. Pat. No. 4,497,741 issued Feb. 5, 1985; U.S. Pat. No. 4,648,992 issued Mar. 10, 1987; and U.K. Pat. No. 1,372,035 published Oct. 30, 1974; U.K. Pat. No. 1,408,144 published Oct. 1, 1975; U.K. Pat. No. 2,159,516 published Dec. 4, 1985; U.K. Pat. No. 1,593,623 published Jul. 22, 1981; E.P. 484,027 A1 published May 6, 1992; WO 91/18006 published Nov. 28, 1991; WO 92/01753 published Feb. 6, 1992; and Japanese Kokai 06-73397 Derwent Abst. No. (94-128933) published Mar. 15, 1994.

In addition to the above cited patent publications, other references describing the synthesis, preparation and properties of phthalocyanines and naphthalocyanines, in corporated herein also by reference; *Phthalocyanines: Properties and Applications*, Leznoff, C. C. and Lever A. B. P. (Eds), VCH, 1989; *Infrared Absorbing Dyes*, Matsuoka, M. (Ed), Plenum, 1990; *Inorg. Chem.*, Lowery, M. J. et al., 4, pg. 128, (1965); *Inorg. Chem.* Joyner R. D. et al., 1, pg. 236, (1962); *Inorg. Chem.*, Kroenke, W. E. et al., 3, 696, 1964; *Inorg. Chem.* Esposito, J. N. et al., 5, pg. 1979, (1966); *J. Am. Chem. Soc.* Wheeler, B. L. et al., 106, pg. 7404, (1984); *Inorg. Chem.* Ford, W. E, et al., 31, pg. 3371, (1992); *Material Science*, Witkiewicz, Z. et al., 11, pg. 39, (1978); *J. Chem. Soc.* Perkin Trans. I, Cook, M. J., et al., pg. 2453, (1988).

SUMMARY OF THE INVENTION

The present invention relates to photodisinfecting and photo anti-microbial compositions comprising:

a) an organosilicon(IV) photosensitizing compound having a Q-band maximum absorption wavelength of 660 nanometers or greater comprising a photosensitizing portion and a solublizing/substrate affinity portion said organosilicon(IV) photosensitizing compound is a phthalocyanine having the formula

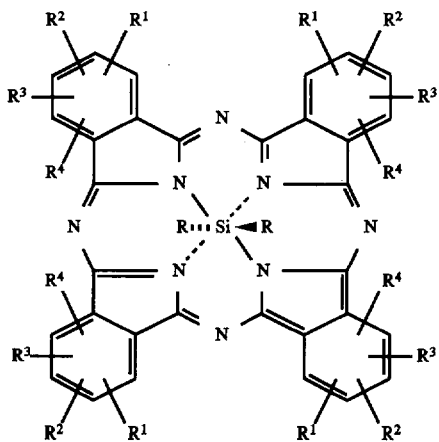

or a naphthalocyanine having the formula:

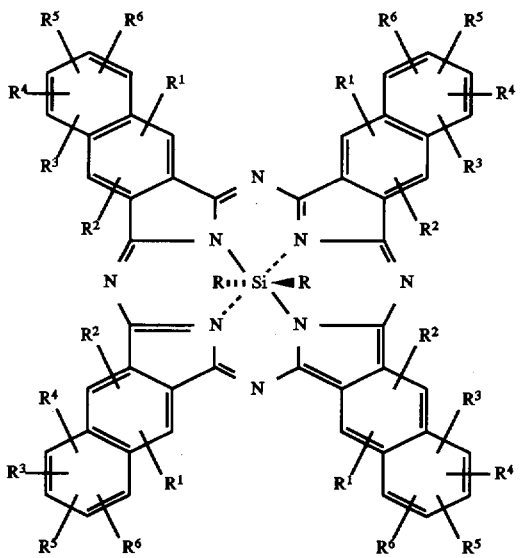

wherein $R^1$, $R^2$, $R^3$, $R^4$, $R^5$, and $R^6$ units are each independently selected from the group consisting of:
a) hydrogen;
b) halogen;
c) hydroxyl;
d) cyano;
e) nitrilo;
f) oximino;
g) $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;
h) halogen substituted $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;
i) polyhydroxyl substituted $C_3$–$C_{22}$ alkyl;
j) $C_1$–$C_{22}$ alkoxy;
k) branched alkoxy having the formula

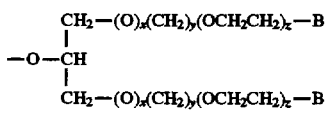

or

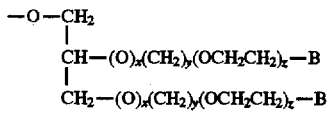

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3^{2-}$M, —$OPO_3^{2-}$M, and mixtures thereof; M is a water soluble cation in sufficient amount to satisfy charge balance; x is 0 or 1, each y independently has the value from 0 to 6, each z independently has the value from 0 to 100;
l) substituted and unsubstituted aryl;
m) substituted and unsubstituted alkylenearyl;
n) substituted and unsubstituted aryloxy;
o) substituted and unsubstituted oxyalkylenearyl;
p) substituted and unsubstituted alkyleneoxyaryl;
q) $C_1$–$C_{22}$ thioalkyl, $C_4$–$C_{22}$ branched thioalkyl, and mixtures thereof;
r) an ester of the formula —$CO_2R^{10}$ wherein $R^{10}$ comprises
  i) $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;
  ii) halogen substituted $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;
  iii) polyhydroxyl substituted $C_3$–$C_{22}$ alkyl;
  iv) $C_3$–$C_{22}$ glycol;
  v) $C_1$–$C_{22}$ alkoxy;
  vi) $C_4$–$C_{22}$ branched alkoxy;
  vii) substituted and unsubstituted aryl;
  viii) substituted and unsubstituted alkylaryl;
  ix) substituted and unsubstituted aryloxy;
  x) substituted and unsubstituted alkoxyaryl;
  xi) substituted and unsubstituted alkyleneoxyaryl; and mixtures thereof;
s) an alkyleneamino unit of the formula

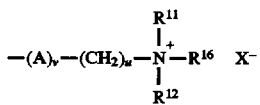

wherein $R^{11}$ and $R^{12}$ comprises $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof; $R^{16}$ comprises:
  i) hydrogen;
  ii) $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;

A units comprise nitrogen or oxygen; X comprises chlorine, bromine, iodine, or other water soluble anion, v is 0 or 1, u is from 0 to 22;
t) an amino unit of the formula

wherein $R^{11}$ and $R^{12}$ comprises $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;
u) an alkylethyleneoxy unit of the formula

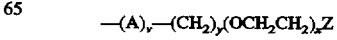

wherein Z comprises:

i) hydrogen;
ii) hydroxyl;
iii) —CO$_2$H;
iv) —SO$_3$-M$^+$;
v) —OSO$_3$-M$^+$;
vi) C$_1$–C$_6$ alkoxy;
vii) substituted and unsubstituted aryl;
viii) substituted and unsubstituted aryloxy;
ix) alkyleneamino; and mixtures thereof;
A units comprise nitrogen or oxygen, M is a water soluble cation, v is 0 or 1, x is from 0 to 100, y is from 0 to 12;
v) substituted siloxy of the formula

—OSiR$^7$R$^8$R$^9$ wherein each R$^7$, R$^8$, and R$^9$ is independently selected from the group consisting of:
i) C$_1$–C$_{22}$ alkyl, C$_4$–C$_{22}$ branched alkyl, C$_2$–C$_{22}$ alkenyl, C$_4$–C$_{22}$ branched alkenyl, and mixtures thereof;
ii) substituted and unsubstituted aryl;
iii) substituted and unsubstituted aryloxy;
iv) an alkylethyleneoxy unit of the formula

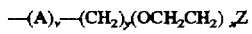
—(A)$_v$—(CH$_2$)$_y$(OCH$_2$CH$_2$)$_z$Z wherein Z comprises:
a) hydrogen;
b) C$_1$–C$_{30}$ alkyl,
c) hydroxyl;
d) —CO$_2$H;
e) —SO$_3$-M$^+$;
f) —OSO$_3$-M$^+$;
g) C$_1$–C$_6$ alkoxy;
h) substituted and unsubstituted aryl;
i) substituted and unsubstituted aryloxy;
j) alkyleneamino; and mixtures thereof;
A units comprise nitrogen or oxygen, M is a water soluble cation, v is 0 or 1, x is from 0 to 100, y is from 0 to 12; and mixtures thereof;
axial R units wherein each R is independently selected from the group consisting of:
a) hydrogen;
b) halogen;
c) hydroxyl;
d) cyano;
e) nitrilo;
f) oximino;
g) C$_1$–C$_{22}$ alkyl, C$_4$–C$_{22}$ branched alkyl, C$_2$–C$_{22}$ alkenyl, C$_4$–C$_{22}$ branched alkenyl, and mixtures thereof;
h) halogen substituted C$_1$–C$_{22}$ alkyl, C$_4$–C$_{22}$ branched alkyl, C$_2$–C$_{22}$ alkenyl, C$_4$–C$_{22}$ branched alkenyl, and mixtures thereof;
i) polyhydroxyl substituted C$_3$–C$_{22}$ alkyl;
j) C$_1$–C$_{22}$ alkoxy;
k) branched alkoxy having the formula

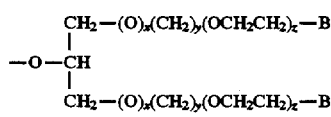

or

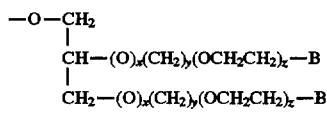

wherein B is hydrogen, hydroxyl, C$_1$–C$_{30}$ alkyl, C$_1$–C$_{30}$ alkoxy, —CO$_2$H, —CH$_2$CO$_2$H, —SO$_3$-M$^+$, —OSO$_3$-M$^+$, —PO$_3^{2-}$M, —OPO$_3^{2-}$M, and mixtures thereof; M is a water soluble cation in sufficient mount to satisfy charge balance; x is 0 or 1, each y independently has the value from 0 to 6, each z independently has the value from 0 to 100;

l) substituted and unsubstituted aryl;
m) substituted and unsubstituted alkylenearyl;
n) substituted and unsubstituted aryloxy;
o) substituted and unsubstituted oxyalkylenearyl;
p) substituted and unsubstituted alkyleneoxyaryl;
q) C$_1$–C$_{22}$ thioalkyl, C$_4$–C$_{22}$ branched thioalkyl, and mixtures thereof;
r) an alkyleneamino unit of the formula

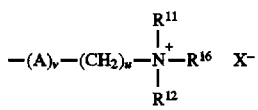

wherein R$^{11}$ and R$^{12}$ comprises C$_1$–C$_{22}$ alkyl, C$_4$–C$_{22}$ branched alkyl, C$_2$–C$_{22}$ alkenyl, C$_4$–C$_{22}$ branched alkenyl, and mixtures thereof; R$^{16}$ comprises:
i) hydrogen;
ii) C$_1$–C$_{22}$ alkyl, C$_4$–C$_{22}$ branched alkyl, C$_2$–C$_{22}$ alkenyl, C$_4$–C$_{22}$ branched alkenyl, and mixtures thereof;
A units comprise nitrogen or oxygen; X comprises chlorine, bromine, iodine, or other water soluble anion, v is 0 or 1, u is from 0 to 22;
s) an amino unit of the formula

—NR$^{11}$R$^{12}$ wherein R$^{11}$ and R$^{12}$ comprises C$_1$–C$_{22}$ alkyl, C$_4$–C$_{22}$ branched alkyl, C$_2$–C$_{22}$ alkenyl, C$_4$–C$_{22}$ branched alkenyl, and mixtures thereof;
t) an alkylethyleneoxy unit of the formula

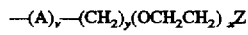
—(A)$_v$—(CH$_2$)$_y$(OCH$_2$CH$_2$)$_z$Z wherein Z comprises:
i) hydrogen;
ii) hydroxyl;
iii) —CO$_2$H;
iv) —SO$_3$-M$^+$;
v) —OSO$_3$-M$^+$;
vi) C$_1$–C$_6$ alkoxy;
vii) substituted and unsubstituted aryl;
viii) substituted and unsubstituted aryloxy;
ix) alkyleneamino; and mixtures thereof;
A comprises nitrogen or oxygen, M is a water soluble cation, v is 0 or 1, x is from 0 to 100, y is from 0 to 12;

u) carboxylate of the formula

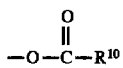

wherein $R^{10}$ comprises:

i) $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;
ii) halogen substituted $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;
iii) poly-hydroxyl substituted $C_3$–$C_{22}$ alkyl;
iv) $C_3$–$C_{22}$ glycol;
v) $C_1$–$C_{22}$ alkoxy;
vi) $C_4$–$C_{22}$ branched alkoxy;
vii) substituted and unsubstituted aryl;
viii) substituted and unsubstituted alkylaryl;
ix) substituted and unsubstituted aryloxy;
x) substituted and unsubstituted alkoxyaryl;
xi) substituted and unsubstituted alkyleneoxyaryl;
xii) alkyleneamino; and mixtures thereof;

v) substituted siloxy of the formula

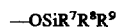

wherein each $R^7$, $R^8$, and $R^9$ is independently selected from the group consisting of:

i) $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;
ii) substituted and unsubstituted aryl;
iii) substituted and unsubstituted aryloxy;
iv) an alkylethyleneoxy unit of the formula

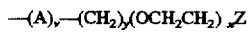

wherein Z comprises:

a) hydrogen;
b) $C_1$–$C_{30}$ alkyl,
c) hydroxyl;
d) —$CO_2H$;
e) —$SO_3$-$M^+$;
f) —$OSO_3$-$M^+$;
g) $C_1$–$C_6$ alkoxy;
h) substituted and unsubstituted aryl;
i) substituted and unsubstituted aryloxy;
j) alkyleneamino; and mixtures thereof;

A units comprise nitrogen or oxygen, M is a water soluble cation, v is 0 or 1, x is from 0 to 100, y is from 0 to 12;

and mixtures thereof; and b) the balance carriers and adjunct ingredients.

All percentages, ratios and proportions herein are by weight, unless otherwise specified. All temperatures are in degrees Celsius (°C.) unless otherwise specified. All documents cited are, in relevant part, incorporated herein by reference.

DETAILED DESCRIPTION OF THE INVENTION

For the purposes of the present invention substituted aryl units are defined as moieties having essentially the formula:

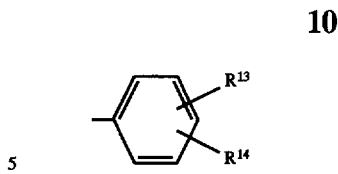

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ wherein each $R^{15}$ is independently hydrogen or $C_1$–$C_4$ alkyl; and mixtures thereof; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like.

For the purposes of the present invention alkylenearyl units are defined as moieties having essentially the formula:

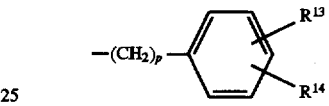

wherein $R^{13}$ and $R^{14}$ are the same as define above, p is from 1 to about 10.

For the purposes of the present invention aryloxy units are defined as moieties having essentially the formula:

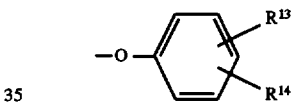

wherein $R^{13}$ and $R^{14}$ are the same as define above.

For the purposes of the present invention alkyleneoxyaryl units are defined as moieties having essentially the formula:

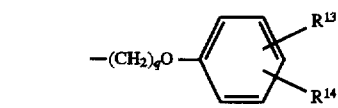

wherein $R^{13}$ and $R^{14}$ are the same as define above, q is from 0 to about 10.

For the purposes of the present invention oxyalkylenearyl units are defined as moieties having essentially the formula:

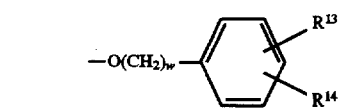

wherein $R^{13}$ and $R^{14}$ are the same as define above, w is from 1 to about 10.

For the purposes of the present invention branched alkoxy units are defined as moieties having essentially the formula

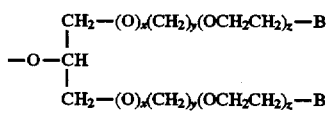

or

-continued

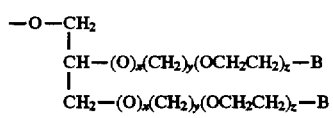

wherein B is hydrogen, hydroxyl, $C_1$-$C_{30}$ alkyl, $C_1$-$C_{30}$ alkoxy, —$CO_2H$, —$CH_2CO_2H$, —$SO_3$-$M^+$, —$OSO_3$-$M^+$, —$PO_3{}^{2-}M$, —$OPO_3{}^{2-}M$, and mixtures thereof; preferably $C_1$-$C_{18}$ alkyl, —$CO_2H$, —$SO_3$-$M^+$, —$OSO_3$-$M^+$, —$PO_3{}^{2-}M$, —$OPO_3{}^{2-}M$; M is a water soluble cation in sufficient amount to satisfy charge balance; x is 0 or 1, each y independently has the value from 0 to 6, each z independently has the value from 0 to 100;

For the purposes of the present invention both substituted and un-substituted aryl, alkylenearyl, aryloxy, oxyalkylenearyl and alkyleneoxyaryl have the indices p, q, and w as defined herein above, and aryl can be any aromatic moiety substituted or unsubstituted, for example, phenyl, naphthyl, thienyl, pyridinyl, etc.

For the purposes of the present invention alkylethyleneoxy units are defined as moieties having essentially the formula:

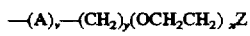

wherein A is the heteroatom nitrogen or oxygen, preferably A is oxygen, the index v is 0 when the heteroatom is absent, v is equal to 1 when the heteroatom is present, Z is hydrogen, $C_1$-$C_6$ alkoxy, aryl, substituted aryl, aryloxy, substituted aryloxy, alkyleneamino, —$SO_3$-$M^+$, —$OSO_3$-$M^+$, —$CO_2H$, and mixtures thereof; x is from 1 to 100 and y is from 1 to 12.

For the purposes of the present invention alkyleneamino units are defined as moieties having essentially the formula:

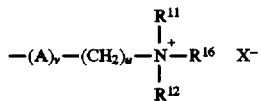

wherein $R^{11}$, and $R^{12}$ are each a $C_1$-$C_{22}$ alkyl, $C_4$-$C_{22}$ branched alkyl, $C_2$-$C_{22}$ alkenyl, $C_4$-$C_{22}$ branched alkenyl, $R^{16}$ is hydrogen, $C_1$-$C_{22}$ alkyl, $C_4$-$C_{22}$ branched alkyl, $C_2$-$C_{22}$ alkenyl, $C_4$-$C_{22}$ branched alkenyl and mixtures thereof, A is the heteroatom nitrogen or oxygen, preferably A is oxygen, the index v is 0 when the heteroatom is absent, v is equal to 1 when the heteroatom is present, X is chloride, bromide, iodide, or other water soluble anion, u is from 0 to 22. Examples of other water soluble anions include organic species such as fumarate, tartrate, oxalate and the like, inorganic species include sulfate, hydrogen sulfate, phosphate and the like.

The present invention provides for photobleaching compositions comprising $Si^{4+}$ organosilicon photosensitizing compounds having a Q-band maximum absorption wavelength of 660 nanometers or greater essentially of the formula

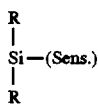

In the above formula the (Sens.) units are bi dentate photosensitizing units which form an essentially planar chelate around the central silicon atom, wherein these (Sens.) units are either phthalocyanines having the formula:

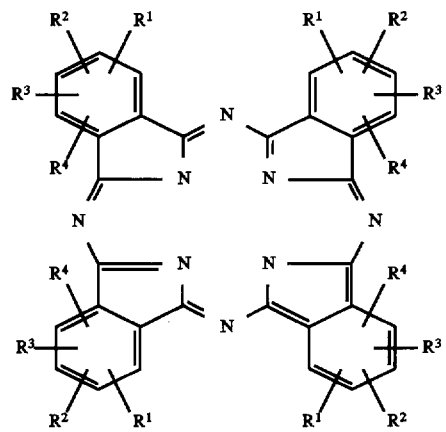

or naphthalocyanines having the formula

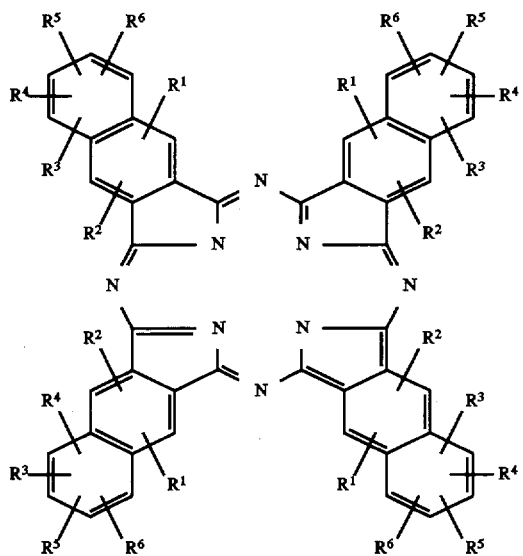

and when the $Si^{4+}$ is combined with the the above described phthalocyanine or naphthalocyanine rings they form the organosilicon compounds having essentially the following formulas

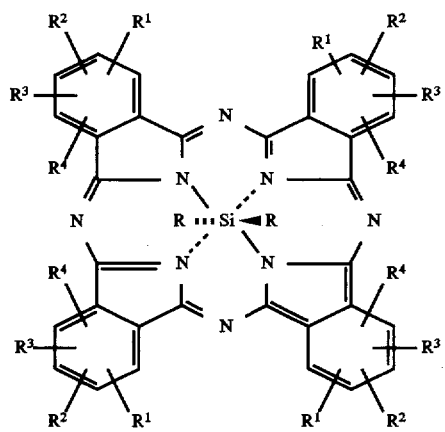

and:

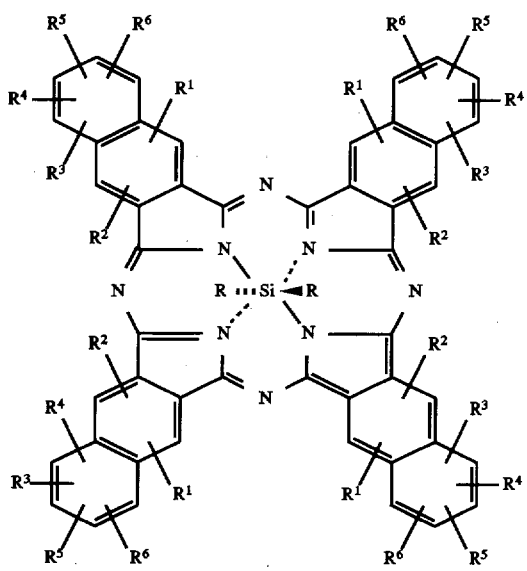

wherein each aromatic ring of the phthalocyanine ring system can be substituted with up to four units, for example, $R^1$, $R^2$, $R^3$, and $R^4$ units, for a maximum of sixteen substitutions per phthalocyanine molecule, and each aromatic ring system of the naphthalocyanine ring system can be substituted with up to six units, for example $R^1$, $R^2$, $R^3$, $R^4$, $R^5$, and $R^6$ units, for a maximum of twenty-four substitutions per naphthalocyanine molecule.

Phthalocyanine and naphthalocyanine ring units

The hydrogen atoms of the phthalocyanine and naphthalocyanine bi-dentate chelant rings are substituted to effect the photochemical properties of the molecules. Phthalocyanines have $R^1$, $R^2$, $R^3$, and $R^4$ units which are capable of substitution and naphthalocyanines have $R^1$, $R^2$, $R^3$, $R^4$, $R^5$, and $R^6$ units capable of substitution. These units are bonded to the phthalocyanine or naphthalocyanine rings and are independently selected from the group consisting of:

a) hydrogen;

b) halogen;

c) hydroxyl;

d) cyano;

e) nitrilo;

f) oximino;

g) $C_1$–$C_{22}$ alkyl, $C_4$–$C_{22}$ branched alkyl, $C_2$–$C_{22}$ alkenyl, $C_4$–$C_{22}$ branched alkenyl;

h) halogen substituted $C_1$–$C_{22}$ alkyl, $C_4$–$C_{22}$ branched alkyl, $C_2$–$C_{22}$ alkenyl, $C_4$–$C_{22}$ branched alkenyl;

i) polyhydroxyl substituted $C_3$–$C_{22}$ alkyl;

j) $C_1$–$C_{22}$ alkoxy, preferably $C_1$–$C_4$ alkoxy, more preferred methoxy;

k) branched alkoxy having the formula

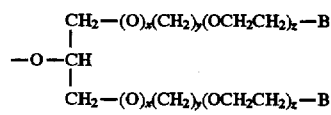

or

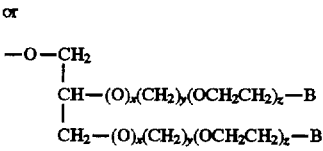

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, preferably from 0 to 6; each z independently has the value from 0 to 100, preferably from 0 to about 10, more preferably from 0 to about 3;

l) aryl, and substituted aryl having essentially the formula:

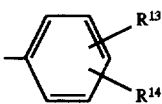

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ wherein each $R^{15}$ is independently hydrogen or $C_1$–$C_4$ alkyl; and mixtures thereof; preferably hydrogen $C_1$–$C_6$ alkyl, —$CO_2$ -$M^+$, —$SO_3$-$M^+$, —$OSO_3$-$M^+$, and mixtures thereof, more preferably $C^{13}$ or $C^{14}$ is hydrogen and the other moiety is $C_1$–$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like;

m) alkylenearyl and substituted alkylenearyl having essentially the formula:

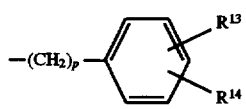

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ wherein each $R^{15}$ is independently hydrogen or $C_1$–$C_4$ alkyl; and mixtures thereof; preferably hydrogen $C_1$–$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$–$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like; p is from 1 to about 10, preferably from 1 to about 3;

n) aryloxy and substituted aryloxy having essentially the formula:

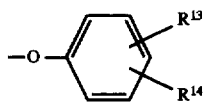

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ wherein each $R^{15}$ is independently hydrogen or $C_1$–$C_4$ alkyl; and mixtures thereof; preferably hydrogen $C_1$–$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$–$C_6$; wherein M is a water soluble cation and X is chlorine, bromine, iodine, or other water soluble union. Examples of other water soluble unions include organic species such as fumarate, tartrate, oxalate and the like, inorganic species include sulfate, hydrogen sulfate, phosphate and the like;

o) alkyleneoxyaryl and substituted alkyleneoxyarylalkyleneoxyaryl units are defined as moieties having essentially the formula:

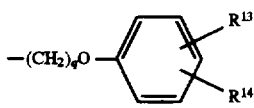

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ wherein each $R^{15}$ is independently hydrogen or $C_1$–$C_4$ alkyl; and mixtures thereof; preferably hydrogen $C_1$–$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$–$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like; q is from 0 to about 10 preferably from about 1 to about 3;

p) oxyalkylenearyl and substituted oxyalkylenearyl having essentially the formula:

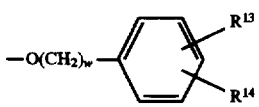

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ each $R^{15}$ is independently hydrogen or $C_1$–$C_4$ alkyl; and mixtures thereof; preferably hydrogen $C_1$–$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$–$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like; w is from 1 to about 10, preferably from about 1 to about 3;

q) $C_1$–$C_{22}$ thioalkyl, $C_4$–$C_{22}$ substituted thioalkyl, and mixtures thereof;

r) ester units of the formula —$CO_2R^{10}$ wherein $R^{10}$ is $C_1$–$C_{22}$ alkyl, $C_4$–$C_{22}$ branched alkyl, $C_2$–$C_{22}$ alkenyl, $C_4$–$C_{22}$ branched alkenyl, all of which can be substituted with halogen; poly-hydroxyl substituted $C_3$–$C_{22}$ alkyl, $C_3$–$C_{22}$ glycol; $C_1$–$C_{22}$ alkoxy, $C_4$–$C_{22}$ branched alkoxy; aryl, substituted aryl, alkylenearyl, aryloxy, alkyleneoxyaryl, alkyleneoxyaryl; preferably $C_1$–$C_{22}$ alkyl, $C_4$–$C_{22}$ branched alkyl, and mixtures thereof;

s) alkyleneamino units having essentially the formula:

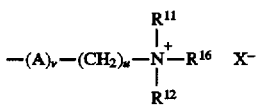

wherein $R^{11}$, and $R^{12}$ are each a $C_1$–$C_{22}$ alkyl, $C_4$–$C_{22}$ branched alkyl, $C_1$–$C_{22}$ alkenyl, $C_4$–$C_{22}$ branched alkenyl, $R^{16}$ is hydrogen, $C_1$–$C_{22}$ alkyl, $C_4$–$C_{22}$ branched alkyl, $C_1$–$C_{22}$ alkenyl, $C_4$–$C_{22}$ branched alkenyl and mixtures thereof, A is the heteroatom nitrogen or oxygen, preferably A is oxygen, the index v is 0 when the heteroatom is absent, v is equal to 1 when the heteroatom is present, preferably v is equal to 0; X is chloride, bromide, iodide, or other water soluble anion, u is from 0 to 22, preferably u is from 3 to about 10. Examples of other water soluble anions include organic species such as fumarate, tartrate, oxalate and the like, inorganic species include sulfate, hydrogen sulfate, phosphate and the like;

t) an amino unit of the formula

wherein $R^{11}$ and $R^{12}$ comprises $C_1$–$C_{22}$ alkyl, $C_4$–$C_{22}$ branched alkyl, $C_2$–$C_{22}$ alkenyl, $C_4$–$C_{22}$ branched alkenyl, and mixtures thereof;

u) alkylethyleneoxy units having essentially the formula:

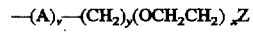

wherein A is the heteroatom nitrogen or oxygen, preferably A is oxygen, the index v is 0 when the heteroatom is absent, v is equal to 1 when the heteroatom is present, Z is hydrogen, $C_1$–$C_6$ alkoxy, aryl, substituted aryl, aryloxy, substituted aryloxy, alkyleneamino, —$SO_3$-$M^+$, —$OSO_3$-$M^+$, —$CO_2H$, and mixtures thereof, preferably hydrogen or $C_1$–$C_6$ alkoxy, more preferably methoxy; x is from 1 to 100, preferably from 0 to about 20, more preferably from 3 to about 10; and y is from 1 to 12, preferably from about 1 to about 5;

v) siloxy and substituted siloxy of the formula —$OSiR^7R^8R^9$ wherein each $R^7$, $R^8$, and $R^9$ is independently selected from the group consisting of $C_2$–$C_8$ alkyl, $C_4$–$C_8$ branched alkyl, $C_1$–$C_8$ alkenyl, $C_4$–$C_8$ branched alkenyl, substituted alkyl, aryl, alkylethyleneoxy units of the formula

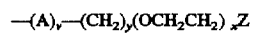

wherein Z is hydrogen, $C_1$–$C_{30}$ alkyl, hydroxyl, —$CO_2H$, —$SO_3$-$M^+$, —$OSO_3$-$M^+$, $C_1$–$C_6$ alkoxy, aryl, substituted aryl, aryloxy, substituted aryloxy alkyleneamino; and mixtures thereof; A units comprise nitrogen or oxygen, M is a water soluble cation, v is 0 or 1, x is from 0 to 100, y is from 0 to 12; and mixtures thereof; and, alkyleneamino units and mixtures thereof.

Preferred $R^1$, $R^2$, $R^3$, $R^4$, $R^5$, and $R^6$ units are $C_1$–$C_{22}$ alkoxy, branched alkoxy having the formula

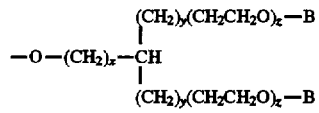

wherein B is hydrogen, $C_1$–$C_{30}$ alkyl, —$CO_2H$, —$SO_3$-$M^+$, —$OSO_3$-$M^+$, —$PO_3^{2-}M$, —$OPO_3^{2-}M$, and mixtures thereof; preferably $C_1$–$C_{18}$ alkyl, —$CO_2H$, —$SO_3$-$M^+$, —$OSO_3$-$M^+$, —$PO_3^{2-}M$, —$OPO_3^{2-}M$; M is a water soluble cation in sufficient amount to satisfy charge balance; x is 0 or 1, each y independently has the value from 0 to 6, preferably from 0 to 6; each z independently has the value from 0 to 100, preferably from 0 to about 10, more preferably from 0 to about 3; and halogen, more preferred $R^1$, $R^2$, $R^3$, $R^4$, $R^5$, and $R^6$ units are methoxy, branched alkoxy and halogen. When the (Sens.) unit is phthalocyanine most preferred $R^1$, $R^2$, $R^3$, and $R^4$ units are methoxy and branched alkoxy. When the (Sens.) unit is naphthalocyanine most preferred $R^1$, $R^2$, $R^3$, $R^4$, $R^5$, and $R^6$ units are chlorine, bromine or iodine.

Axial R units

The compounds useful for the present invention also comprise axial R units bonded directly to the central silicon atom, wherein R is independently selected from the group consisting of:

a) hydrogen;
b) halogen;
c) hydroxyl;
d) cyano;
e) nitrilo;
f) oximino;
g) $C_1$–$C_{22}$ alkyl, $C_4$–$C_{22}$ branched alkyl, $C_2$–$C_{22}$ alkenyl, $C_4$–$C_{22}$ branched alkenyl;
h) halogen substituted $C_1$–$C_{22}$ alkyl, $C_4$–$C_{22}$ branched alkyl, $C_1$–$C_{22}$ alkenyl, $C_4$–$C_{22}$ branched alkenyl;
i) polyhydroxyl substituted $C_3$–$C_{22}$ alkyl;
j) $C_1$–$C_{22}$ alkoxy, preferably $C_1$–$C_4$ alkoxy, more preferred methoxy;
k) branched alkoxy having the formula

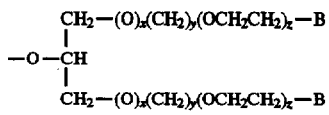

or

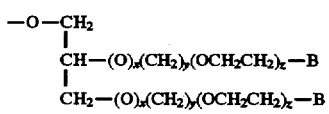

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, preferably from 0 to 6; each z independently has the value from 0 to 100, preferably from 0 to about 10, more preferably from 0 to about 3;

l) aryl, and substituted aryl having essentially the formula:

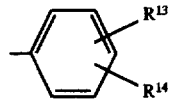

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ each $R^{15}$ is independently hydrogen or $C_1$–$C_4$ alkyl; and mixtures thereof; preferably hydrogen $C_1$–$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$–$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like;

m) alkylenearyl and substituted alkylenearyl having essentially the formula:

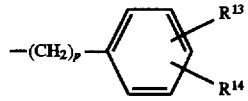

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ wherein each $R^{15}$ is independently hydrogen or $C_1$–$C_4$ alkyl; and mixtures thereof; preferably hydrogen $C_1$–$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$–$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like; p is from 1 to about 10, preferably from 1 to about 3;

n) aryloxy and substituted aryloxy having essentially the formula:

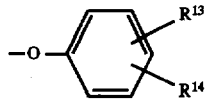

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_1$–$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ each $R^{15}$ is independently hydrogen or $C_1$–$C_4$ alkyl; and mixtures thereof; preferably hydrogen $C_1$–$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$–$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like;

o) alkyleneoxyaryl and substituted alkyleneoxyarylalkyleneoxyaryl units are defined as moieties having essentially the formula:

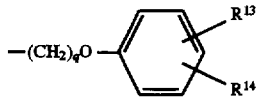

wherein $R^{13}$ and $R^{14}$ are independently selected from the group consisting of hydrogen, $C_1$-$C_6$ alkyl, $C_2$-$C_6$ alkenyl, $C_1$-$C_6$ alkoxy, $C_1$-$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ each $R^{15}$ is independently hydrogen or $C_1$-$C_4$ alkyl; and mixtures thereof; preferably hydrogen $C_1$-$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$-$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like; q is from 0 to about 10 preferably from about 1 to about 3;

p) oxyalkylenearyl and substituted oxyalkylenearyl having essentially the formula:

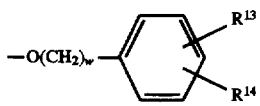

wherein $R^{13}$ and $R^{14}$ are independently selected from the group consisting of hydrogen, $C_1$-$C_6$ alkyl, $C_2$-$C_6$ alkenyl, $C_1$-$C_6$ alkoxy, $C_1$-$C_6$ branched alkoxy, halogen, morpholino, cyano, nitrilo, —$CO_2$-$M^+$, —$SO_3$-$M^+$, —$OSO_3$-$M^+$, —$N(R^{15})_2$, and —$N^+(R^{15})_3X^-$ wherein each $R^{15}$ is independently hydrogen or $C_1$-$C_4$ alkyl; and mixtures thereof; preferably hydrogen $C_1$-$C_6$ alkyl, —$CO_2$-$M^+$, —$SO_3$-$M^+$, —$OSO_3$-$M^+$, and mixtures thereof, more preferably $C^{13}$ or $C^{14}$ is hydrogen and the other moiety is $C_1$-$C_6$; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like; w is from 1 to about 10, preferably from about 1 to about 3;

q) $C_1$-$C_{22}$ thioalkyl, $C_4$-$C_{22}$ substituted thioalkyl, and mixtures thereof;

r) alkyleneamino units having essentially the formula:

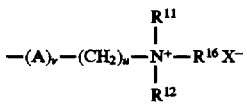

wherein $R^{11}$, and $R^{12}$ are each a $C_1$-$C_{22}$ alkyl, $C_4$-$C_{22}$ branched alkyl, $C_2$-$C_{22}$ alkenyl, $C_4$-$C_{22}$ branched alkenyl, $R^{16}$ is hydrogen, $C_1$-$C_{22}$ alkyl, $C_4$-$C_{22}$ branched alkyl, $C_2$-$C_{22}$ alkenyl, $C_4$-$C_{22}$ branched alkenyl and mixtures thereof, A is the heteroatom nitrogen or oxygen, preferably A is oxygen, the index v is 0 when the heteroatom is absent, v is equal to 1 when the heteroatom is present, preferably v is equal to 0; X is chloride, bromide, iodide, or other water soluble anion, u is from 0 to 22, preferably u is from 3 to about 10. Examples of other water soluble anions include organic species such as fumarate, tartrate, oxalate and the like, inorganic species include sulfate, hydrogen sulfate, phosphate and the like;

s) an amino unit of the formula

wherein $R^{11}$ and $R^{12}$ comprises $C_1$-$C_{22}$ alkyl, $C_4$-$C_{22}$ branched alkyl, $C_2$-$C_{22}$ alkenyl, $C_4$-$C_{22}$ branched alkenyl, and mixtures thereof;

t) alkylethyleneoxy units having essentially the formula:

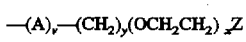

wherein A is the heteroatom nitrogen or oxygen, preferably A is oxygen, the index v is 0 when the heteroatom is absent, v is equal to 1 when the heteroatom is present, Z is hydrogen, $C_1$-$C_6$ alkoxy, aryl, substituted aryl, aryloxy, substituted aryloxy, alkyleneamino, —$SO_3$-$M^+$, —$OSO_3$-$M^+$, —$CO_2H$, and mixtures thereof, preferably hydrogen or $C_1$-$C_6$ alkoxy, more preferably methoxy; x is from 1 to 100, preferably from 0 to about 20, more preferably from 3 to about 10; and y is from 1 to 12, preferably from about 1 to about 5;

u) carboxylate units of the formula

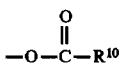

wherein $R^{10}$ is $C_1$-$C_{22}$ alkyl, $C_4$-$C_{22}$ branched alkyl, $C_2$-$C_{22}$ alkenyl, $C_4$-$C_{22}$ branched alkenyl, all of which can be substituted with halogen; poly-hydroxyl substituted $C_3$-$C_{22}$ alkyl, $C_3$-$C_{22}$ glycol; $C_1$-$C_{22}$ alkoxy, $C_4$-$C_{22}$ branched alkoxy; substituted and unsubstituted aryl, substituted and unsubstituted alkylenearyl, substituted and unsubstituted aryloxy, substituted and unsubstituted alkyleneoxyaryl, substituted and unsubstituted alkyleneoxyaryl; preferably $C_1$-$C_{22}$ alkyl, $C_4$-$C_{22}$ branched alkyl, and mixtures thereof;

v) siloxy and substituted siloxy of the formula —$OSiR^7R^8R^9$ wherein each $R^7$, $R^8$, and $R^9$ is independently selected from the group consisting of $C_1$-$C_8$ alkyl, $C_4$-$C_8$ branched alkyl, $C_2$-$C_8$ alkenyl, $C_4$-$C_8$ branched alkenyl, substituted alkyl, aryl, alkylethyleneoxy units of the formula

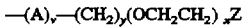

wherein Z is hydrogen, $C_1$-$C_{30}$ alkyl, hydroxyl, —$CO_2H$, —$SO_3$-$M^+$, —$OSO_3$-$M^+$, $C_1$-$C_6$ alkoxy, aryl, substituted aryl, aryloxy, substituted aryloxy alkyleneamino; and mixtures thereof; A units comprise nitrogen or oxygen, M is a water soluble cation, v is 0 or 1, x is from 0 to 100, y is from 0 to 12; and mixtures thereof; and, alkyleneamino units and mixtures thereof.

Preferred R units are the polyhydroxyl substituted $C_3$-$C_{22}$ alkylene moieties that are essentially polyglycols of the formula —$(CHOH)_nCH_2OH$, wherein the value of n is from 2 to 21; preferred polyhydroxy substituted alkylenes are those polyhydroxy glycols essentially of the formula

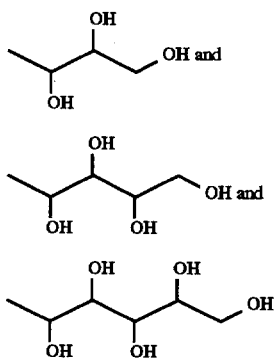

wherein the stereochemical configuration of these polyhydroxyl moieties are equivalent for the purposes of the present invention.

Most prefered axial R units are branched alkoxy having the formula

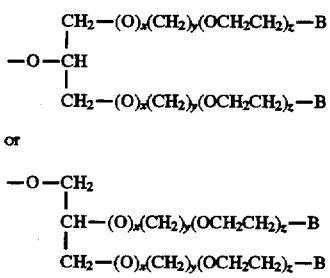

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3^{2-}M$, —$OPO_3^{2-}M$, and mixtures thereof; M is a water soluble cation in sufficient mount to satisfy charge balance; x is 0 or 1, each y independently has the value from 0 to 6, preferably from 0 to 6; each z independently has the value from 0 to 100, preferably from 0 to about 10, more preferably from 0 to about 3.

When compounds of the present invention have present one or more substituent $R^1$, $R^2$, $R^3$, and $R^4$, units, as in the case of phthalocyanine, or $R^1$, $R^2$, $R^3$, $R^4$, $R^5$, and $R^6$ units, as in the case of naphthalocyanines, the exact orientation of the substituents may not be exactly known. However, for the purposes of the compounds of the present invention, certain equivalencies of substitution exist. For example, the two units of the following formula

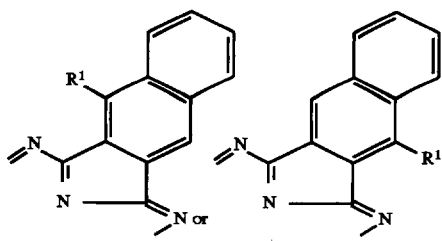

which contain the same $R^1$ substitution, are equivalent for the purposes of the present invention and the selection of either one structure over the other will not effect the desired properties of the molecule described herein.

In addition, compounds containing the substitution represented by the following formulas

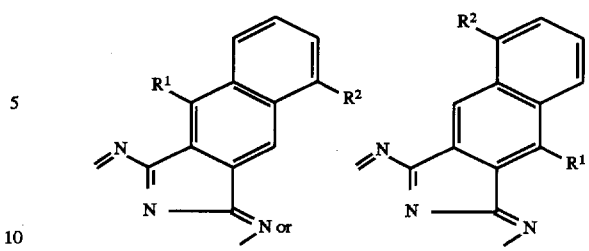

which contain the same $R^1$ and $R^2$ unit substitutions, are also equivalent for the purposes of the present invention and the selection of either one structure over the other will not effect the desired properties of the molecule described herein. The above examples, however, are only representative of the total number of equivalent structure examples that will be recognized by those skilled in the art.

Compounds useful for the present invention having substituted one or more $R^1$, $R^2$, $R^3$, and $R^4$, unit, as in the case of phthalocyanine, or $R^1$, $R^2$, $R^3$, $R^4$, $R^5$, and $R^6$ unit, as in the case of naphthalocyanines, which have their substitutions oriented in a manner described essentially by the following formula

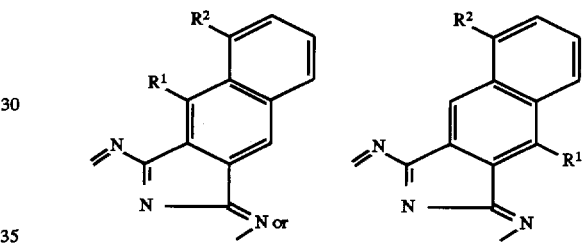

are not equivalent for the purposes of the present invention and would each constitute separate compounds regardless of the fact that the $R^1$ and $R^2$ units are equivalent. The above example does not exhaust the number of non-equivalent structures that are possible using any combination of $R^1$, $R^2$, $R^3$, $R^4$, $R^5$, and $R^6$ units recognized by those skilled in the art.

Solublizing axial R units, are bonded directly to the central silicon atom, which for the purposes of the present invention is a $Si^{4+}$ atom, and occupy a position axial to the essentially planar (Sens.) unit. The utility of each R unit is primarily directed to the solubility properties of the compounds of the present invention and each R unit can be chosen independently of the other. The selection of an R unit can be made, in addition to, or in lieu of, solubility requirements, and be totally directed instead to the "substantivity" or "non-substantivity" of the compound. R units are essentially nonionic, cationic, or anionic units.

Below is an example of a preferred "substantive" embodiment (has an affinity for surfaces, e.g. fabric) of the present invention comprising a phthalocyanine ting system wherein at least one of the $R^1$, $R^2$, $R^3$, and $R^4$ units of each aromatic moiety is methoxy, each R group comprises an ethyleneoxy unit of essentially the formula

wherein for each R unit Z is methoxy and x is 7.2 thereby giving the moiety an average ethoxylation value of 7.2.

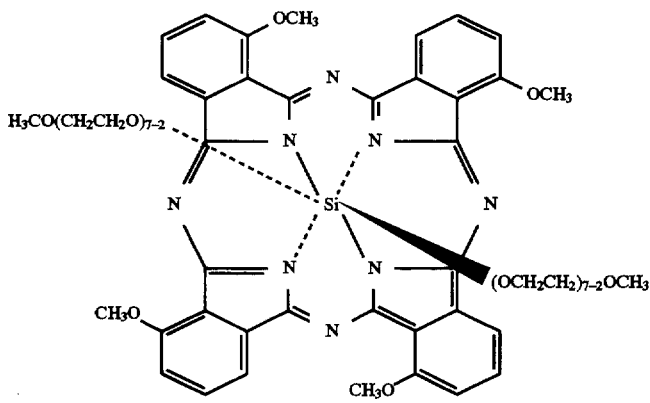

Below is an example of a more preferred "substantive" embodiment (has an affinity for surfaces, e.g. fabric) of the present invention comprising a phthalocyanine ring system wherein at least two of the $R^1$, $R^2$, $R^3$, and $R^4$ units of each aromatic moiety is methoxy, each R group comprises an ethyleneoxy unit of essentially the formula

wherein for each R unit Z is methoxy and x is 7.2 thereby giving the moiety an average ethoxylation value of 7.2.

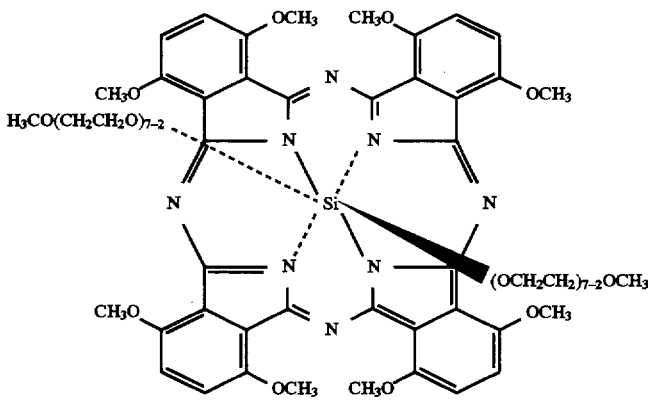

Below is an example of a "non-substantive" embodiment (charged R units reduces the affinity for surfaces, e.g. fabric) of the present invention comprising a naphthalocyanine ring system wherein at least two of the $R^1$, $R^2$, $R^3$, $R^4$, $R^5$, and $R^6$ units of each aromatic moiety are chlorine, one R group comprises an siloxy unit essentially the formula —$OSiR^7R^8R^9$ wherein $R^7$ and $R^8$ units are methyl and $R^9$ is essentially of the formula

wherein Z is —$SO_3$-$M^+$, M is sodium and y is equal to six; the second axial R unit is methoxy.

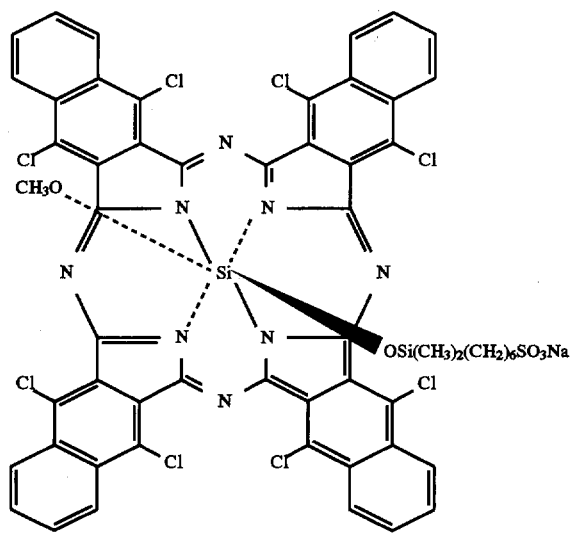

Below is an example of a preferred "non-substantive" embodiment (charged R units reduces the affinity for surfaces, e.g. fabric) of the present invention comprising a naphthalocyanine ring system wherein at least one of the $R^1$, $R^2$, $R^3$, $R^4$, $R^5$, and $R^6$ units of each aromatic moiety is bromine, and the R groups comprise an siloxy unit essentially the formula —$OSiR^7R^8R^9$ wherein $R^7$ and $R^8$ units are methyl and $R^9$ is essentially of the formula —$(CH_2)_yZ$ wherein Z is —$SO_3$-$M^+$, M is sodium and y is equal to six.

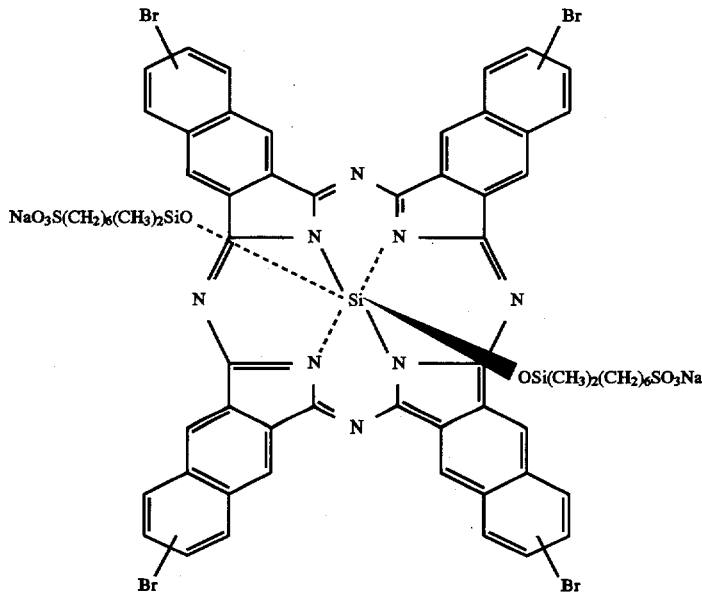

The compounds of the present invention can be modified to have a wide range of surface affinities. Molecules can be made "substantive" or "non-substantive" by the choice of axial R units. The term "substantivity" as defined herein is the property which allows the photodisinfectanting agent to successfully contact a particular targeted surface. For example, the axial groups R, hereinafter defined in the specification, may be selected to provide compatibility of the photodisinfecting compound with a synthetic fabric, a durable surface such as ceramic tile, or in general any fabric, article of manufacture or situs that is to be a target of photo disinfecting.

For example, the R unit is matched to the structural properties of either the targeted material (i.e. fabric) or to the targeted substrate (i.e. microbe). The option to tailor the properties of the R unit to the material such as a disposable paper article of manufacture, is due to the ability to select R units independently of effecting the phthalocyanine or naphthalocyanine ring thereby leaving the photophysics unaffected.

"Non-substantive" molecules are desirable for applications where the photosensitizing compound must remain in the liquor rather than becoming attracted to a particular surface, i.e. swimming pool photodisinfectants. While not wishing to be limited by way of example, the substitution of a charged moiety for an R unit will act to make the compound repel any surface that is slightly charged or does not have an affinity for the chosen R unit.

While not wishing to be limited by theory, the mechanism by which photodisinfecting occurs is a diffusion controlled process and therefore the compounds of the present invention by there unique structural qualities are well suited for high efficiency singlet oxygen production. Effective photo disinfecting is predicated on the production of a molecule of singlet oxygen, a theory which has been extensively studied and is well understood by those skilled in the art of photo disinfecting. Because the singlet oxygen species is short-lived and its photo-energy transfer is diffusion controlled, that is, singlet oxygen rapidly reacts with receptor molecules in the surrounding molecular milieu, having the photosensitizing molecule in proximity to the situs of the microbe or similar object to be "attacked" is of primary advantage.

The molecules of the present invention because of the ability of the formulator to achieve a rational degree of "substantivity" can direct the molecules of the present invention to any desired surface. The additional ability to prevent layering and stacking of photosensitizing molecules due to the axial nature of the R units, provides for an efficient mono-layer to be applied to the "situs of action". For example, an embodiment of the present invention for killing microbes absorbed onto a fabric due to exposure of the fabric to body fluids or other sources of micro organisms, will have the requirements that the organosilicon photosensitizing compound have an affinity for the fabric surface (substantivity for the surface), that the photo disinfecting compound be close to the desired site of action (achieved by manipulation of one or more R units) for "high molecular efficiency". Clearly it would be advantageous given these requirements to deposit a "monolayer" of the photo disinfectant, this requires that the Q-band be sufficiently above 700 nm to prevent the eye detecting the photo disinfectant.

Another advantage of the present invention is the fact that each R unit may be directed toward a separate desired property and the molecules of the present invention can therefore be thought of as being "sided". For example, one axial R unit may be direct toward increased solubility while the other axial R group may be chosen for its ability to provide increase substantivity with respect to a given surface.

However, the ability to provide "substantivity" to a molecule of the present invention is matched by the desire and ability of the formulator to provide "non-substantivity" to examples of photodisinfectants of the present invention. The use of a non-substantive embodiment of the present invention would be applicable when using a method of the present invention for the purpose of disinfecting a swimming pool with a photo disinfectant of the present invention. A substantive material would bind or adhere to the sides of the pool and have less effect than a non-substantive material that would remain evenly dispersed in solution.

The term "low hue" as used herein and throughout the specification refers to photodisinfectants that have a lambda max of their Q-band above about 660 nm and are therefore only slightly perceptible to the human eye. "Low hue" is a term similar to "low color" but the term low hue connotes the fact that the Q-band is a range and not a single discreet wavelength and the lower end of this band may be perceptible in part only to a relatively few people, rather than referring to the level or intensity or the amount of color (hue) produced per molecule.

The term "low hue", as used in the present specification and as further defined hereinafter, refers to the visible perception created when organosilicon compounds of the present invention are applied to a solid white background, it will appear colorless, due to the fact that their Q-band absorption maxima ($\lambda_{max}$) is at a wavelength such that it is either invisible or only slightly visible to the naked eye, the cutoff wavelength for human visible perception being approximately 660 nm. However, some "low hue" organosilicon photosensitizing compounds of the present invention will appear more visible than others depending on the type of surface on which they are used or the "hue" may be effected by the presence of adjunct ingredients such as fluorescent whitening agents, dyes colorants or the wavelength range of the light that is present.

Some compounds of the present invention having a $\lambda_{max}$ of from 660 to about 700 nm may be desirable in applications where the inherent color of the molecule serves as an indicator of the presence of the photo disinfecting agent. For example, effluent waste treated with 660 to 700 nm materials of the present invention may impart a color that serves to insure the formulator that the effluent still contains the photodisinfectant.

The present invention also relates to a process for carrying out a photosensitized reaction or a reaction catalyzed by singlet oxygen, wherein one or more phthalocyanine or naphthylocyanine compounds in the presence of oxygen, are brought into contact with the medium in which or on which the said reaction is to take place, or are incorporated in this medium, and are irradiated with light.

While not wishing to be limited by theory, the photodisinfectants of the present invention are more "adjustable" with regard to the efficiency of photophysics. The formulator, now unburdened in the choice of substituent on the phthalocyanine or naphthalocyanine ring system because solubility considerations are a perview of the axial R moieties, can fully concentrate on optimizing the photophysics of the compound.

It has long been known that certain large conjugated adducts, such as phthalocyanine and naphthalocyanine rings, can absorb light quanta and form electronically excited species (singlet and triplet) and that these species can be quenched by oxygen to yield 'excited oxygen species'. A particularly preferred 'excited oxygen species' is singlet oxygen which is most reliably formed by the quenching of the triplet state of a photosensitizer, such as a phthalocyanine, by molecular oxygen. It is therefore an aim of the photodisinfectant formulator to produce compounds that favor the formation of the triplet state.

When a photo sensitizer is irradiated with light, the singlet energy state that results undergoes a variety of processes i.e. re-emission of light (fluorescence). The most important process with regard to photobleaching via singlet oxygen is inter system crossing (ISC). This is the mechanism by which the singlet state is converted to the triplet state within a molecule. In general, the efficiency of this process is discussed in terms of quantum yield, i.e. the number of photons absorbed that lead to the desired triplet excited state. The present invention provides for increased photobleaching by modifying the efficiency of inter system crossing from the singlet state to the triplet state. The molecules of the present invention, can be modified by the formulator to increase the quantum efficiency by which the triplet state is formed. Surprisingly, the formulator can manipulate the substituents according to the present invention to increase the contribution certain substituents have on the "heavy atom effect", a term familiar to those skilled in the art. The selection of a moiety for its "heavy atom effect" can be made independently of other factors, for example, without undue concern for solubility factors. This is because the choice of axial R groups for solubility will have no bearing on the changes made to the phthalocyanine or naphthalocyanine ring system.

The Q-band, as well understood by those skilled in the art, is the low energy absorption band that is associated with excitation of an electron to its first singlet state. For example, in the case of the phthalocyanines and napthalocyanines of the present invention, the wavelength associated with this absorption is typically from 600 to 800 nanometers. This range encompasses wavelengths of both the visible and the near infrared spectrum. A weaker absorption band relative to the Q-band for the compounds of the present invention can be found at shorter wavelengths that comprise the UV and visible spectrum. This second absorption band is known as the B-band. Unlike the Q-band, the B-band represents the excitement of an electron to its second singlet state. The present invention concerns the stronger Q-band absorption which is associated with the strong color of phthalocyanines, naphthalocyanines and the like.

The determination of the value of the Q-band wavelength and whether a shift occurs in this wavelength when a particular moiety ($R^1$, $R^2$, $R^3$, $R^4$, $R^5$ or $R^6$ unit) replaces a hydrogen atom on the phthalocyanine or naphthalocyanine ring is straight-forward. Typically, a solution having a concentration of approximately $1\times10^{-6}$M of the phthalocyanine or naphthalocyanine to be measured is prepared using a suitable solvent (e.g. dimethylformamide) which contains 1 wt % triton X-100. A UV/visible spectrum is then obtained and the Q-band $\lambda_{max}$ is recorded. This value is the "substrate $\lambda_{s-max}$". A spectrum for the material prior to introduction of the substituent group is obtained in the same manner. This value is the "reference $\lambda_{r-max}$". The two spectra are compared and the resulting measured values are placed into the following equation $$\text{wavelength red shift} = \Delta\lambda_{max} = \lambda_{s-max} - \lambda_{r-max}$$

wherein if the number obtained is greater than or equal to 1, then the substituent group has produced a positive red shift of at least one nanometer and is a material suitable for use in the embodiments of the present invention. Those skilled in the art of photochemistry will recognize that the term $\Delta\lambda_{max}$ is a dimensionless number and for the purposes of the present invention when the Q-band of the modified photodisinfectant is measured in nanometers and compared to the un-modified photodisinfectant, the Q-band of the modified disinfectant will have an increase in wavelength of at least one nanometer. If the material of interest is not soluble in dimethylformamide other suitable solvents may be used. Aggregation of the phthalocyanine or naphthalocyanine compounds, leading to a false value for the Q-band wavelength, can be avoided by the addition of triton X-100.

Quantum yields and excited state energies are well known to those skilled in the art and the procedures for the determination of triplet quantum yield and like photophysical parameters are thoroughly described in the following references Bonnet, R.; McGarvey, D. J.; Harriman, A.; Land, E. J.; Truscott, T. G.; Winfield, *U-J. Photochem. Photobiol.* 1988, 48 (3), pg. 271–6; Davila, J., Harriman, A., Gulliya, K. S., *Photochem. Photobiol.*, 1991, 53 (1), pg. 1–11; Davila, J., Harriman, A., *Photochem. Photobiol.*, 1989, 50 (1), pg. 29–35; Charlesworth, P., Truscottt, T. G., Brooks, R. C., Wilson, B. C., *J. Photochem, Photobiol.*, part B 1994, 26 (3), pg. 277–82; Zhang, X., Xu, H., *J. Chem. Soc.*, Faraday Trans., 1993, 89 (18), pg. 3347–51; Simpson, M. S. C., Beeby, A.; Bishop, S. M., MacRobert, A. J., Parker, A. W., Phillips, D., *Proc. SPIE-int. Soc. Opt. Eng.*, 1992, 1640, pg. 520–9; Phillips, D., *Pure Appl. Chem.*, 1995, 67 (1), pg. 117–26; Wilkinson, F., Helman, W. P., Ross, A. B., *J. Phys. Chem. Ref. Data*, 1993, 22 (1), pg. 113–262; Lever, A. P. B., Licoccia, S., Magnell, K., Minor, P. C., Ramaswamy, B. S., *Adv. Chem. Ser.*, 1982, 201, pg. 237–52; West, M. A., *Creat. Detect. Excited State*, 1976, 4, pg. 217–307; Ford, W. E., Rihter, B. D., Kenney, M. E., Rodgers, M. A. J., *Photochem. Photobiol.*, 1989, 50 (3), pg. 277–282; Firey, P. A., Ford, W. E., Sounik, J. R., Kenney, M. E., Rodgers, A. J. R., *J. Am. Chem. Soc.*, 1988, 110, pg. 7626–7630; Firey, P. A., Rodgers, M. A. J., *Photochem. Photobiol.*, 1987, 45 (4), pg. 535–8; all of which are incorporated by reference in their entirety.

For the purposes of the present invention the delta triplet yield is determined according to the following equation $$\text{triplet state yield increase} = \Delta\Phi_{trip} = \Phi_{trip-substrate} - \Phi_{trip-reference}$$

wherein the values for $\Phi_{trip-substrate} - \Phi_{trip-reference}$ can be obtained by any of the methods described in the references cited herein above. When the value for $\Delta\Phi_{trip}$ is a number greater than or equal to 1, the substitution made therein for a hydrogen atom on the (Sens.) unit of the photosensitizer is suitable for use in the embodiments of the present invention.

In addition, modifications to "hueing", that is the inherent color or lack of color, can be manipulated without regard to the properties brought to bear by the choice of axial R group.

In particular, the present invention relates to process for controlling microorganisms in or on organic or inorganic substrates or for protecting the latter against attack by microorganisms, wherein the textiles or the substrates to be freed from or protected against micro-organisms, are treated with phthalocyanines or naphthalocyanies of the present invention, in the presence of water and while being irradiated by light.

In order to develop their antimicrobial activity, the phthalocyanine or naphthalocyanine compounds of the present invention require the presence of oxygen and water as well as irradiation with light. Treatment is therefore generally carried out in aqueous solution or on moist substrates, and the source of oxygen used is the oxygen dissolved in the water or atmospheric oxygen.

The irradiation can be effected by means of an artificial source of light or by means of sunlight. A good effect is achieved for example, by means of light within the rang between about 300 and 2500 nm, preferably from about 300 to about 1200 nm. Thus irradiation can be carried out, for example, using a commercially available incandescent lamp. The intensity of the illumination can vary within wide limits, It depends on the concentration of active substance on the nature of the substrate or on the substance additionally present whcih influence the light yield. A further parameter which can be varied is the exposure time, i.e. for the same effect exposure must be longer at a lower light intensity than at a higher intensity. In general, depending on the field of use, exposure time of a few minutes up to a few hours is possible.

If the method is carried out in an aqueous medium (for example the sterilization of textiles), the irradiation with light can either be carried out directly in the treatment medium by means of an artificial source of light mounted inside or outside the medium or the substrates, in a moist state, can subsequently either be irradiated, again by means of an artificial source of light, or can be exposed to sunlight. Good antimicrobial effects of the present compounds can be achieved even with very low concentrations of active substance, for example at 0.001 ppm. Depending on the field of use and on the phthalocyanine or naphthylocyanine derivative employed, a concentration between 0.005 and 100, preferably 0.01 and 50 ppm is preferable.

The methods of the present invention can also be accomplished in solvent based carriers or in low aqueous solutions. For the purpose of the present invention the term low aqueous means that water is added to a carrier system to modify the properties of the carrier and not solely for the purpose of solublizing the substrate. For example, solvents that are capable of holding solublized oxygen as well as forming a miscible system with water are preferred. Non-limiting examples of these solvents are butoxy propoxy propanol (BPP), which is available in commercial quantities as a mixture of isomers in about equal amounts, methoxy propoxy propanol (MPP), ethoxy propoxy propanol (EPP), and propoxy propoxy propanol (PPP). Embodiments of the present invention which comprise these non-classical aqueous compositions are most useful when the photo disinfectant must be applied to a woven fabric or surface that contains agents which repel water and moisture.

The phthalocyanine or naphthalocyanine compounds of the present invention employed in the process according to the invention have an extremely broad spectrum of activity against microorganisms. Thus it is possible to control, in particular, Gram-positive bacteria, but also Gram-negative bacteria by means of the process according to the present invention. An action against fungi and yeast is also observed.

Substances which increase the action can also be added in the process according to the invention, inter alia electrolytes, for example inorganic salts, for instance sodium chloride, potassium chloride, sodium sulfate, potassium sulfate, sodium acetate ammonium acetate, alkali metal phosphates and alkali metal tripolyphosphates, especially sodium chloride and sodium sulfate. These salts can be added to the agents according to the invention or can be added directly in the application method, so that they are present in the application solution in a concentration of, preferably 0.1 to 10%, by weight.

By virtue of the broad spectrum of action mentioned against microorganisms, the process according to the invention or the agents according to the invention can be employed in number of fields of use, examples which are listed below.

The sterilization of paper articles of manufacture or aseptic barriers of synthetic or natural original may be mentioned as an important application. Thus, material to be washed in the household or in industry can be disinfected by means of the methods of the present invention. The material to be washed can be treated for this purpose in the manner mentioned above with aqueous solutions of the phthalocyanines or naphthylocyanines of the present invention while being irradiated with light. The phthalocyanine and naphthylo-cyanines can advantageously be present in the treatment medium in a concentration of from 0.001 to about 1000 ppm, preferably from about 0.01 to about 100 ppm, more preferably from about 0.1 to about 50 ppm.

The sterilization can be carried out advantageously together with the washing process. For this purpose, the material to be washed is treated with a wash medium containing customary detergent substances, one or more phthalocyanines or naphthylocyanines according to the present invention and, if desired, inorganic salts and/or other adjunct materials having antimicrobial properties. The washing process con be carried out manually, for example in a tub, or can be carded out in a washing machine. The necessary exposure to light can be effected during the washing process by means of suitable light sources, or the moist material being washed can also, subsequently, for example during drying, either be exposed to a suitable artificial source of light or simply exposed to sunlight, for example line drying.

The method according to the present invention can also be used to impart an antimicrobial finish to textiles, since the phthalocyanine and naphthalocyanine derivatives are readily adsorbed by the fibers and ensure a long lasting effect.

A further field of use for the method according to the present invention and for the agents according to the invention is the disinfecting of hospital linen, medical articles for daily use and pieces of equipment and floors walls and furniture (surface disinfecting) both generally and particularly in hospitals. The disinfecting of hospital linen can be carried out in the manner described above for general material to be washed. The other articles, and also the surfaces of floors and walls, can be treated with aqueous solutions containing the phthalocyanine or naphthalocyanine compounds according to the present invention and, in the course thereof or subsequently, can be exposed to suitable sources of light. The disinfecting solutions can, in addition also comprise detergent substances, other compounds having a microbial action and/or inorganic salts.

Surface disinfecting at a situs can be achieved, for example by applying (for example by spraying) to the appropriate surface, an aqueous solution of the phthalocyanine or naphthalocyanine compound according to the present invention, this solution preferably comprising from about 0.001 ppm to about 1000 ppm, by weight of active substance. The solution Can also comprise, in addition, other customary additives, for example wetting agents, dispersing agents or emulsifiers, detergent substances and, if desired inorganic salts. After this solution has been applied and the situs is exposed to a source of microorganisms, i.e. body fluids, the surface is simply exposed to sunlight or, if required, it can in addition be irradiated by means of an artificial source of light, for example and incandescent lamp. It is advisable to keep the surface moist by addition of an aqueous solution during the exposure to light.

What is meant by the term aqueous solution is a solution that comprises predominately water, however the formulator may include adjunct materials as well as a surfactant to aid in removal of the "treated" microorganisms during rinsing or subsequent cleaning. The presence of an aqueous solution facilitates the production of singlet oxygen due to the higher concentration of oxygen in water than in air.

The methods according to the invention and/or the agents according to the present invention can also be employed with advantage for sterilizing or disinfecting swimming baths. For this purpose it is advantageous to add one or more of the compound of the present invention, preferably in an mount of from 0.001 to about 50, preferably 0.01 to about 1 ppm to the water in the swimming pool. Exposure is effected merely by means of sunlight. If desired, additional exposure by means of built-in lamps can be provided. It is possible, by means of the process described, to keep the water of swimming pool and other baths free from undesirable germs and to maintain the quality of the water in an excellent state. One advantage the compounds of the present invention have over typical chlorine based swimming pool disinfectants, is the fact that the chlorine agents are transitory in nature and must be replenished usually on a daily basis, whereas the compounds of the present invention can be prepared so as not to degrade for a longer period of time, typically up to one week. Also one atom of hypochlorite in the chlorine based sanitizers is expended per each oxidation that is utilized for anti microbial action, whereas the molecules of the present invention continuously produce singlet oxygen.

The present invention also provides for a method of making water potable for human use. A compound of the present invention is placed into the water to be made potable at a level of at least 0.001 ppm and the water is subsequently exposed to sunlight or to a source of incandescent light preferably in the range of from about 300 to about 1200 nm. The present invention also relates to a method for maintaining water in a potable state for use by human, in that the holding tank or pond is supplied with at least 0.001 ppm of a photo disinfectant of the present invention and subsequently the water is exposed to a source of light as described herein. The amount of material suitable to provide potable water or to maintain water potable will be predicated on the type and level of photodisinfecting necessary and the time of exposure to light will also depend on these factors.

The method of the present invention can also be used for sterilizing effluents from sewage treatment plants. This is accomplished by adding to the effluent, for example 0.0001 to about 100 ppm of one or more of the compounds of the present invention. Irradiation is advantageously effected by means of sunlight; if desired, additional irradiation can be carried out by means of artificial sources of light.

The disinfecting compositions of the present invention optionally comprise detersive surfactants, examples of which are, anionic, cationic, nonionic, amphoteric and zwitterionic, however the formulator is not limited to these examples or combinations thereof. The surfactants are present from about 0% to about 95%, preferably from about 5% to about 30%, by weight of the composition.

The disinfecting compositions of the present invention optionally comprise other anti microbial agents or indicators which, when placed into contact with water, indicate the presence of active organosilicon photodisinfectants of the present invention.

The swimming pool disinfectant compositions of the present invention optionally comprise detersive surfactants, examples of which are, anionic, cationic, nonionic, ampho-teric and zwitterionic, however the formulator is not limited to these examples or combinations thereof. The surfactants are present from about 0% to about 50%, preferably from about 5% to about 30%, by weight of the composition.

ADJUNCT MATERIALS

Surfactant—The instant photo disinfectant compositions contain from about 0% to about 60% by weight of a surfactant selected from the group consisting of anionic, nonionic, ampholytic and zwitterinonic surface active agents. For liquid systems, surfactant is preferably present to the extent of from about 0.1% to 20% by weight of the composition. For solid (i.e. granular) and viscous semi-solid (i.e. gelatinous, pastes, etc.) systems, surfactant is preferably present to the extent of from about 1.5% to 30% by weight of the composition.

Nonlimiting examples of surfactants useful herein typically at levels from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)$ $CH_3$ and $CH_3(CH_2)_y(CHOSO_3^-M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("AE$_x$S"; especially EO 1–7 ethoxy sulfates), $C_{10}$–$C_{18}$ alkyl alkoxy carboxylates (especially the EO 1–5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) gluca-mide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are described further herein and are listed in standard texts.

Anionic surfactants can be broadly described as the water-soluble salts, particularly the alkali metal salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic synthetic detergents which can form the surfactant component of the compositions of the present invention are the sodium or potassium alkyl sulfates, especially those obtained by sulfating the higher alcohols (C8–18 carbon atoms) produced by reducing the glycerides of tallow or coconut oil; sodium or potassium alkyl benzene sulfonates, in whcih the alkyl group contains from about 9 to about 15 carbon atoms, (the alkyl radical can be a straight or branched aliphatic chain); sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid ester of the reaction product of one mole of a higher fatty alcohol (e.g. tallow or coconut alcohols) and about 1 to about 10 moles of ethylene oxide; sodium or potassium salts of alkyl phenol ethylene oxide ether sulfates with about 1 to about 10 units of ethylene oxide per molecule and in which the alkyl radicals contain from 8 to 12 carbon atoms; the reaction products of fatty acids are derived from coconut oil sodium or potassium salts of fatty acid amides of a methyl tauride in which the fatty acids, for example, are derived from coconut oil and sodium or potassium beta-acetoxy- or beta-acetamido-alkanesulfonates where the alkane has from 8 to 22 carbon atoms.

Additionally, secondary alkyl sulfates may be used by the formulator exclusively or in conjunction with other surfactant materials and the following identifies and illustrates the differences between sulfated surfactants and otherwise conventional alkyl sulfate surfactants. Non-limiting examples of such ingredients are as follows.

Conventional primary alkyl sulfates, such as those illustrated above, have the general formula ROSO3–M+ wherein R is typically a linear C8–22 hydrocarbyl group and M is a water solublizing cation. Branched chain primary alkyl sulfate surfactants (i.e., branched-chain "PAS") having 8–20 carbon atoms are also know; see, for example, Eur. Pat. Appl. 439,316, Smith et al., filed Jan. 21, 1991.

Conventional secondary alkyl sulfate surfactants are those materials which have the sulfate moiety distributed randomly along the hydrocarbyl "backbone" of the molecule. Such materials may be depicted by the structure

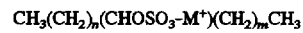

wherein m and n are integers of 2 of greater and the sum of m+n is typically about 9 to 17, and M is a water-solublizing cation.

The aforementioned secondary alkyl sulfates are those prepared by the addition of $H_2SO_4$ to olefins. A typical synthesis using alpha olefins and sulfuric acid is disclosed in U.S. Pat. No. 3,234,258, Morris, issued Feb. 8, 1966 or in U.S. Pat. No. 5,075,041, Lutz, issued Dec. 24, 1991. The synthesis conducted in solvents which afford the secondary (2,3) alkyl sulfates on cooling, yields products whcih, when purified to remove the unreacted materials, randomly sulfated materials, unsulfated by-products such as C10 and higher alcohols, secondary olefin sulfonates, and the like, are typically 90+% pure mixtures of 2- and 3- sulfated materials (some sodium sulfate may be present) and are white, non tacky, apparently crystalline, solids. Some 2,3-disulfates may also be present, but generally comprise no more than 5% of the mixture of secondary (2,3) alkyl mono-sulfates. Such materials are available as under the name "DAN", e.g., "DAN 200" from Shell Oil Company.

Bleaching Agents and Bleach Activators—The detergent compositions herein may optionally contain bleaching agents or bleaching compositions containing a bleaching agent and one or more bleach activators. When present, bleaching agents will typically be at levels of from about 1% to about 30%, more typically from about 5% to about 20%, of the detergent composition, especially for fabric laundering. If present, the amount of bleach activators will typically be from about 0.1% to about 60%, more typically from about 0.5% to about 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches other than the hypohalite (e.g. hypochlorite) bleaches. Perborate (e.g., mono- or tetrahydrate sodium salts) and percarbonate bleaches can be used herein.

Another category of bleaching agent that can be used without restriction encompasses percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxydodecanedioic acid. Such bleaching agents are disclosed in U.S. Pat. No. 4,483,781, Hartman, issued Nov. 20, 1984, U.S. patent application 740,446, Burns et al, filed Jun. 3, 1985, European Patent Application 0,133,354, Banks et al, published Feb. 20, 1985, and U.S. Pat. No. 4,412,934, Chung et al, issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Peroxygen bleaching agents can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONE, manufactured commercially by DuPont) can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

Mixtures of bleaching agents can also be used.

Peroxygen bleaching agents, the perborates, the percarbonates, etc., are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915, 854, issued Apr. 10, 1990 to Mao et al, and U.S. Pat. No. 4,412,934. The nonanoyloxybenzene sulfonate (NOBS) and tetraacetyl ethylene diamine (TAED) activators are typical, and mixtures thereof can also be used. See also U.S. Pat. No. 4,634,551 for other typical bleaches and activators useful herein.

Highly preferred amido-derived bleach activators are those of the formulae:

wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. A leaving group is any group that is displaced from the bleach activator as a consequence of the nucleophilic attack on the bleach activator by the perhydrolysis anion. A preferred leaving group is phenyl sulfonate.

Preferred examples of bleach activators of the above formulae include (6-octanamido-caproyl) oxybenzenesulfonate, (6-nonanamidocaproyl) oxybenzenesulfonate, (6-decanamido-caproyl) oxybenzenesulfonate, and mixtures thereof as described in U.S. Pat. No. 4,634,551, incorporated herein by reference.

Another class of bleach activators comprises the benzoxazin-type activators disclosed by Hodge et al in U.S. Pat. No. 4,966,723, issued Oct. 30, 1990, incorporated herein by reference. A highly preferred activator of the benzoxazin-type is:

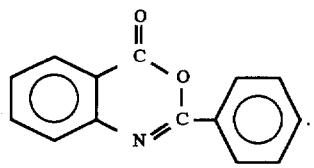

Still another class of preferred bleach activators includes the acyl lactam activators, especially acyl caprolactams and acyl valerolactams of the formulae:

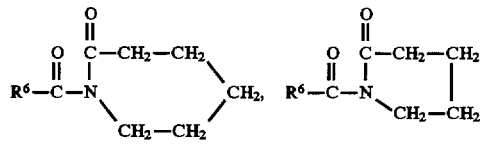

wherein $R^6$ is H or an alkyl, aryl, alkoxyaryl, or alkaryl group containing from 1 to about 12 carbon atoms. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, incorporated herein by reference, which discloses acyl caprolactams, including benzoyl caprolactam, adsorbed into sodium perborate.

As a practical matter, and not by way of limitation, the compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 500 ppm, of the catalyst species in the laundry liquor.

Buffers—Buffers can be included in the formulations herein for a variety of purposes. One such purpose is to adjust the pH to optimize the effect of the axial R group with respect to "non-substantive" embodiments. Buffers may be included to stabilize the adjunct ingredients with respect to extended shelf life or for the purpose of maintaining compatibility between various aesthetic ingredients. Non-limiting examples of such suitable buffers are potassium carbonate, sodium carbonate, and sodium bicarbonate, however, the formulator is not restricted to these examples or combinations thereof.

The compositions herein can optionally include one or more other detergent adjunct materials or other materials for assisting or enhancing cleaning and disinfecting performance, treatment of the surface to be disinfected, or to modify the aesthetics of the composition (e.g., perfumes, colorants, dyes, etc.). The following are illustrative examples of such adjunct materials but are not meant to be exclusive or limiting in scope.

Chelating Agents—The photo disinfectant compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that certain chelating agents will interact with photodisinfectants of the present invention to increase their absorbency in the visible light spectrum. This is a process that is due to the ability of chelating agents to help effect the "substantiveness" of the compounds of the present invention.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions Inert Salts. The inert salts (filler salts) used in the compositions of the present invention can be any water-soluble inorganic or organic salt or mixtures of such salts which do not destabilize any surfactant present. For the purposed of the present invention, "water-soluble" means having a solubility in water of at least 1 gram per 100 grams of water at 20° C. Examples of suitable salts include various alkali metal and/or alkali earth metal sulfate, chlorides, borates, bromides, fluorides, phosphates, carbonates, bicarbonates, citrates, acetates, lactates, etc.

Specific examples of suitable salts include sodium sulfate, sodium chloride, potassium chloride, sodium carbonate, potassium sulfate, lithium chloride, lithium sulfate, tripotassium phosphate, sodium borate, potassium bromide, potassium fluoride, sodium bicarbonate, magnesium sulfate, magnesium chloride, sodium citrate, sodium acetate, magnesium lactate, sodium fluoride. The preferred salts are inorganic salts preferably the alkali metal sulfates and chlorides. Particularly preferred salts, because of their low cost are sodium sulfate and sodium chloride. The salts are present in the compositions at levels of from 0% to 40%, preferably 10% to 20%.

Example 1

Preparation of 1,4-Dimethoxy-2,3-dicyanobenzene

Dimethyl sulfate (15 mL, 0.16 mol) and anhydrous potassium carbonate (24 g, 0.17 mol) are added to a solution of 2,3-dicyanohydroquinone (3.0 g, 0.019 mol) in 100 mL 2-butanone. The reaction mixture is refluxed for 18 hr. under a stream of argon, cooled to room temperature and the resulting solid is collected by filtration. The residue is added to water (100 mL) to dissolve the potassium carbonate and the resulting insoluble material is collected by filtration and dried under vacuum to yield 3.10 g (88%), m.p. 276°–280° C., $^1$H NMR (DMSO-$d_6$) in ppm, $\delta$=7.63 (s, 2H), 3.93 (s, 6H).

Example 2

Preparation of octamethoxy phthalocyanine di-lithium salt

Lithium methoxide (6.05 g, 0.16 mol) is added to a solution of 1,4-dimethoxy-2,3-dicyanobenzene (10 g, 0.05 mol) in 100 mL anhydrous methanol. The reaction mixture is pressurized to approximately 2000–2400 psi with nitrogen gas, heated to 120° C. for 6 hr., cooled to room temperature and vented to atmospheric pressure. The resulting gray/green solid is collected by filtration and dried under vacuum to yield 7.08 g (70%). Q-band $\lambda_{max}$ at 714 nm (DMF).

Example 3

Preparation of octamethoxy phthalocyanine p-Toluene sulfonic acid (15.73 g, 91 mmol) is added to a solution of octamethoxy phthalocyanine di-lithium salt (7.0 g, 9.1 mmol) in 100 mL anhydrous DMF at 50° C. The reaction mixture is stirred at 50° C. 8 hr. under a stream of argon, cooled to approximately 10° C. for 2 hr. and the resulting purple solid is collected by filtration and dried under vacuum to yield 4.91 g (71%). Q-band $\lambda_{max}$ at 764 nm (DMF).

Example 4

Preparation of silicon (IV) octamethoxyphthalocyanine dichloride

Silicon tetrachloride (8 mL, 31.8 mmol) is added to a frozen mixture of octamethoxy phthalocyanine (1.0 g, 0.66 mmol) in 60 mL anhydrous pyridine. The reaction mixture is pressurized to ~2000–2400 psi with nitrogen gas, heated to 180° C. for 24 hr., cooled to room temperature and vented to atmospheric pressure. The product is precipitated by the addition of water and the resulting solid is collected by filtration. The filtrate is dissolved in methanol, precipitated by the addition of 1N hydrochloric acid and collected by filtration. The product is purified by silica gel chromatography using methylene chloride as the elutant. Yield of green product is 0.55 g (49%). Q-band $\lambda_{max}$ at 730 nm (DMF).

Example 5

Preparation of phthalocyanine di-lithium salt

Phthalonitrile (6.4 g, 0.05 mol) is added to 100 mL of refluxing anhydrous butanol containing lithium metal (1.11 g, 0.16 mol). The reaction mixture is refluxed 2 hr. under a stream of argon, cooled to room temperature and the resulting solid is collected by filtration. The blue solid is dried under vacuum to yield 4.26 g (65%).

Example 6

Preparation of phthalocyanine p-Toluene sulfonic acid (13.14 g 76 mmol) was added to a solution of phthalocyanine di-lithium salt (4.0 g, 7.6 mmol) in 100 mL anhydrous DMF at 50° C. The reaction mixture is stirred at 50° C. for 8 hr. under stream of argon, cooled to approximately 10° C. and held at that temperature for 2 hr. The resulting blue solid is collect by filtration and dried to yield 2.96 g (76%). Q-band $\lambda_{max}$ at 659 and 690 nm (DMF).

Example 7

Preparation of silicon (IV) phthalocyanine dichloride

Silicon tetrachloride (8 mL, 31.8 mmol) is added to a frozen mixture of phthalocyanine (0.68 g, 1.32 mmol) in 60 mL anhydrous pyridine. The reaction mixture is pressurized to approximately 2000–2400 psi with nitrogen gas, heated to 180° C. for 24 hr., cooled to room temperature and vented to atmospheric pressure. The reaction product is precipitated by the addition of water and collected by filtration. The filtrate is dissolved in methanol, re-precipitated by the addition of 1N hydrochloric acid and collected by filtration. The product is purified by silica gel chromatography using methylene chloride as the elutant. Yield of blue colored product is 0.44 g (55%). Q-band $\lambda_{max}$ at 670 nm (DMF).

Example 8

Preparation of tetrabromonaphthalocyanine di-lithium salt

Lithium methoxide (6.05 g, 0.16 mol) is added to a solution of 6-bromonapthalene-2,3-dicarbonitrile (1 g, 4 mmol) in 100 mL anhydrous methanol. The reaction mixture is pressurized with nitrogen gas to approximately 2000–2400 psi, heated to 120° C. for 6 hr., then cooled to room temperature. The precipitate is collected by filtration and dried under vacuum to yield approximately 0.4 g (39%).

Example 9

Preparation of tetrabromonaphthalocyanine p-Toluene sulfonic acid (15.73 g, 91 mmol) is added to a solution of tetrabromonaphthalocyanine di-lithium salt (0.3 g, 0.3 mmol) in 100 mL of anhydrous DMF at 50° C. The reaction mixture is stirred at 50° C. of 8 hr. under a stream of argon, cooled to approximately at 10° C. and held for 2 hr. after which the precipitated solid is collected by filtration. The solid is dried under vacuum to yield 0.25 g (83%). Q-band $\lambda_{max}$ at 782 nm (DMF).

Example 10

Preparation of tetra-t-butylphthalocyanine di-lithium salt

Lithium methoxide (6.05 g, 0.16 mol) is added to a solution of 4-t-butylphthalonitrile (1 g, 5.4 mmol) in 100 mL of anhydrous methanol. The reaction mixture is pressurized with nitrogen gas to approximately 2000–2400 psi, heated to 120° C. for 6 hr., then cooled to room temperature. The resulting precipitate is collected by filtration and dried under vacuum to yield 0.8 g (79%).

Example 11

Preparation of tetra-t-butylphthalocyanine p-Toluene sulfonic acid (15.73 g, 91 mmol) is added to a solution of tetra-t-butylphthalocyanine di-lithium salt (0.5 g, 0.6 mmol) in 100 mL of anhydrous DMF at 50° C. The reaction mixture is stirred at 50° C. 8 hr. under a stream of argon, cooled to approximately at 10° C. and held for 2 hr. after which the precipitated solid is collected by filtration. The solid is dried under vacuum to yield 0.35 g (70%). Q-band $\lambda_{max}$ at 680 nm (DMF).

Example 12

Preparation of 1,4-Dipropoxy-2,3-dicyanobenzene

Propyl iodide (15 mL, 0.16 mol) and anhydrous potassium carbonate (24 g, 0.17 mol) are combined with to a solution of 2,3-dicyanohydroquinone (3.0 g, 0.019 mol) in 100 mL of 2-butanone. The reaction mixture is refluxed for 18 hr. under a stream of argon, cooled to room temperature and the solid collected by filtration. The residue is then added to water (100 mL) to dissolve the potassium carbonate and the resulting solid is collected by filtration and dried under vacuum to yield 3.4 g (74%).

Example 13

Preparation of tetrapropoxyphthalocyanine di lithium salt

Tetrapropoxyphthalocyanine di lithium salt is prepared in the manner described above in Example 2 where 1,4-dipropoxy-2,3-dicyanobenzene is substituted for 1,4-dimethoxy-2,3-dicyanobenzene as the starting material. A yield 52% is typically obtained.

Example 14

Preparation of tetrapropoxyphthalocyanine

Tetrapropoxyphthalocyanine was prepared in the manner described above in Example 3 where tetrapropoxyphthalocyanine di lithium salt is substituted for tetramethoxyphthalocyanine as the starting material. A yield of 73% is typically obtained. Q-band $\lambda_{max}$ at 760 nm.

Example 15

Preparation of silicon (IV) phthalocyanine di-(PEG 350 mono-methyl ether)

Silicon (IV) phthalocyanine dichloride (2 g of an 85% sample, 2.78 mmol) is added to a refluxing solution of 40 g of PEG 350 mono-methyl ether in 100 mL of anhydrous DMF. Refluxing is continued for 48 hr. under argon blanketing, then the reaction mixture is cooled to room temperature and the DMF removed under reduced pressure. The resulting 44.21 g of blue oil comprised 7.78% of the desired material. Q-band $\lambda_{max}$ at 682 nm (water).

Example 16

Preparation of silicon (IV) phthalocyanine di-propoxide

Silicon (IV) phthalocyanine dichloride (0.20 g of 85% active, 0.278 mmol) is added to refluxing anhydrous n-propanol (25 mL). Refluxing is continued for an additional 48 hr. under argon blanketing, the reaction mixture is then cooled to room temperature and the solvent removed to afford 0.25 g of a blue solid. Q-band $\lambda_{max}$ at 672 nm (DMF).

Example 17

Preparation of silicon (IV) phthalocyanine di-(p-phenol sulfonate, sodium salt)

Silicon (IV) phthalocyanine dichloride (0.02 g of 85% active, 0.278 mmol) is added to a refluxing solution of anhydrous di-sodium phenol sulfonate (0.12 g, 0.56 mmol) in 100 mL of anhydrous DMF. Refluxing is continued for an additional 96 hr. under argon blanketing, then the reaction is cooled to room temperature and the DMF is removed under reduced pressure. Yield of blue solid is 0.31 g. Q-band $\lambda_{max}$ at 674 nm (DMF).

Example 18

Preparation of silicon (IV) octanemethoxyphthalocyanine di-(PEG 350 monomethyl ether)

The procedure as described in Example 15 is used with 2.0 gm of silicon (IV) octamethoxyphthalocyanine dichloride as the starting material. The resultant green oil comprised 6% of the desired product. Q-band $\lambda_{max}$ at 736 nm (DMF).

Example 19

Preparation of 1,3-di-methoxy-3,6-di-iminoisoindoline from 1,4-di-methoxy-2,3-di-cyanobenzene

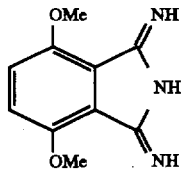

Anhydrous ammonia is bubbled into a solution comprising 1,4-di-methoxy-2,3-di-cyanobenzene (10 g, 53.2 mmol), sodium methoxide (85 mg, 1.6 mmol) and mL of anhydrous methanol for 30 minutes at room temperature. The reaction mixture is then brought to reflux for 3.5 hr. with the continued addition of ammonia then cooled to room temperature and the product collected by filtration. Yield is 4.68 g (43%).

Example 20

Preparation of octamethoxy silicon (IV) phthalocyanine dichloride from 1,3-di-methoxy-3,6-di-iminoisoindoline Silicon tetrachloride (3.59 g, 21.1 mmol) is added to a solution of 1,3-di-methoxy-3,6-diiminoisoindoline (3 g, 14.6 mmol) in 25 mL of anhydrous quinoline at room temperature. The reaction mixture is then slowly brought to reflux over a period of 1.5 hr. then maintained at reflux another half hour. The reaction mixture is subsequently cooled to 100° C. and the crude product removed by filtration. The product is purified by silica gel chromatography with methylene chloride as elutant. Yield of green solid is 1.71 g (55%).

Example 21

Preparation of octamethoxy silicon (IV) phthalocyanine dichloride from octamethoxy phthalocyanine di-lithium salt Silicon tetrachloride (2.22 g, 13.0 mmol) is added to a solution of octamethoxy phthalocyanine di-lithium salt (1 g, 1.3 mmol) in 50 mL of anhydrous nitrobenzene. The reaction mixture is pressurized with nitrogen gas to approximately 2000–2400 psi, heated to 120° C. for 24 hr. The crude product is precipitated by the addition of 400 mL of anhydrous diethyl ether and the resulting solid is collected by filtration. Purification by silica gel chromatography using methylene chloride as eluant affords 0.57 g of a green solid (51%).

Example 22

Preparation of silicon (IV) terta-t-butylphthalocyanine dichloride

The procedure as described in Example 20 is used with 0.5 g of tetra-t-butylphthalocyanine di-lithium salt (as prepared in example 10) as the starting material. A 50% yield of the desired product is obtained. Q-band $\lambda_{max}$ at 700 nm (DMF).

Example 23

Preparation of silicon (IV) tetra-t-butylphthalocyanine dipropoxide

The procedure as described in Example 16 is used with 0.2 g of silicon (IV) tetra-t-butylphthalocyanine (as in Example 22) as starting material. An 80% yield of the desired product is obtained. Q-band $\lambda_{max}$ at 690 nm (propanol).

Example 24

Preparation of 1,2-di-cyano-4,5-di-chloro-3,6-hyrdroquinone from 1,2-di-cyano-4,5-di-chloro-3,6-benzenequinone Sodium bisulfite (34.4 g, 0.33 mol) is added to a solution of 1,2-di-cyano-4,5-di-chloro-3,6-benzenquinone (25 g, 0.11 mol) in 300 mL of water. The reaction mixture is stirred at room temperature for 3 hr. The product is collected by filtration and dried to yield 23.01 g (91.3%).

Example 25

Preparation of 1,2-di-cyano-4,5-di-chloro-3,6-di-methoxybenzene from 1,2-di-cyano-4,5-di-chloro-3,6-hydroquinone The procedure as described in example 1 above is used to provide a yield of 85% of the desired material.

Example 26

Preparation of Octachloro-octamethoxyphthalocyanine di lithium salt from 1,2-di-cyano-4,5-di-chloro-3,6-di-methoxybenzene 1,2-dicyano-4,5-dichloro-3,6-dimethoxybenzene (6.0 g, 23.3 mmol) is added to a refluxing solution of lithium metal (0.65 g, 93.4 mmol) in 75 mL of anhydrous methanol. The reaction mixture is refluxed for 24 hr under argon blanketing and cooled to room temperature. The resulting green solid is collected by filtration to afford 3.98 g (66%). Q-band $\lambda_{max}$ at 692 (DMF).

Example 27

Preparation of silicon (IV) octachloro-octamethoxy phthalocyanine dichloride

The procedure as described in Example 20 is used with 1 g of octachloro-octamethoxyphthalocyanine di lithium salt as the starting material. A yield of 63% of the desired product is obtained. Q-band $\lambda_{max}$ at 730 nm (DMF).

Example 28

Bromination of silicon (IV) naphthalocyanine dichloride

N-bromosuccinimide (0.559 g, 3.1 mmol) is added in 3 equal portions over 8 hour intervals to a solution of silicon (IV) naphthalocyanine dichloride (0.25 g, 0.26 mmol) in 100 mL of anhydrous DMF at 70° C. The reaction mixture is then stirred at 70° C. for 48 hr. under a stream of argon, cooled to room temperature and the solvent removed under reduced pressure. The residue that is obtained is stirred in 100 mL of anhydrous methanol for 18 hr. at room temperature. The product is collected by filtration and dried to yield 0.189 g (77%). Elemental analysis confirms the addition of 1.2 equivalents of bromine.

Example 29

Preparation of silicon (IV) bromonaphthalocyanine di-(PEG 2000 monomethyl ether)

The procedure as described in Example 15 is used with 0.1 g of the brominated silicon (IV) naphthalocyanine dichloride (as in example 27) as starting material and PEG 2000 mono methyl ether. The resultant green solid comprised approximately 0.03% of the desired material. Q-band $\lambda_{max}$ at 780 nm (DMF).

Example 30

Preparation of silicon (IV) tetrabromonaphthalocyanine dichloride

The procedure as described in Example 20 is used with 0.2 g of tetrabromonaphthalocyanine di lithium salt as starting material. A 40% yield is obtained of the desired product. Q-band $\lambda_{max}$ at 790 nm (DMF).

Example 31

Preparation of silicon (IV) tetrabromonaphthalocyanine di-(PEG 2000 monomethylether)

The procedure as described in Example 15 is used with 0.1 g of silicon (IV) tetrabromonaphthalocyanine dichloride (as in Example 28) and PEG 2000 monomethyl ether in plllace of PEG 350 as in the earlier examples. The resultant green solid contained approximately 0.03% of the desired material. Q-band $\lambda_{max}$ at 780 nm (DMF).

Example 32

Preparation of octamethoxy silicon (IV) phthalocyanine dihydroxide

Octamethoxy silicon (IV) phthalocyanine dichloride (0.2 g, 0.26 μmol) is added to a refluxing solution of sodium methoxide (0.8 g, 0.15 μmole) in 15 mL of 95:5 ethanol/water. The reaction mixture is refluxed for 4 hours and cooled to room temperature. The resulting blue green precipitate is collected by filtration to afford 0.174 g (92%). Q-band $\lambda_{max}$ at 734 nm (DMF).

Example 33

Preparation of di-(dimethyl-n-octadecyl) silicon (IV) octamethoxyphthalocyanine Silicon (IV) octamethoxyphthalocyanine dichloride (0.1 g, 0.12 μmol), dimethyl-n-octadecylchlorosilane (0.1 g, 0.3 μmol) and dry tributylamine is refluxed in nitrobenzene for 6 hours. The solution obtained is allowed to cool and filtered. The filtrate was poured into ethanol/water and the product separated and the resulting solid collected by filtration to afford 0.14 g (80%). Q-band $\lambda_{max}$ at 735 nm (DMF).

Example 34

Preparation of Glycerol-di-(Triethylene glycol methyl ether)

To a suspension of sodium hydride (20.4 g, 0.85 moles) in anhydrous dioxane (500 mL) at cooled to about 10° C. under stream of argon is added triethylene glycol monomethyl ether (131.4 g, 0.80 moles) over a period of about 1 hour. The mixture is allowed to warm to room temperature and is subsequently refluxed for 1 hour. After warming to room temperature epichlorohydrin (37.0 g, 0.40 moles) is added. The solution is heated over a period of 2 hours until reflux temperature and then refluxing is continued for an additional 48 hours. After cooling, the solvent is removed in vacuo. The resulting solid is slurried in ether (500 mL), cooled to about 10° C. and then 10% HCl (75 mL) is added over about 0.5 hour. The aqueous layer is decanted and the organic phase extracted with two additional portions of acid. The three aqueous extracts are combined, saturated with NaCl and extracted x4 with 50 mL portions of chloroform. The combined chloroform extracts are dried (MgSO$_4$) and concentrated to yield 97.17 g of a brown oil. The product is used without further purification.

Example 35

Preparation of Glycerol-di-(Diethylene glycol methyl ether)

To a suspension of sodium hydride (20.4 g, 0.85 moles) in anhydrous dioxane (500 mL) at cooled to about 10° C. under stream of argon is added diethylene glycol monomethyl ether (96.12 g, 0.80 moles) over a period of about 1 hour. The mixture is allowed to warm to room temperature and is subsequently refluxed for 1 hour. After warming to room temperature epichlorohydrin (37.0 g, 0.40 moles) is added. The solution is heated over a period of 2 hours until reflux temperature and then refluxing is continued for an additional 48 hours. After cooling, the solvent is removed in vacuo. The resulting solid is slurried in ether (500 mL), cooled to about 10° C. and then 10% HCl (75 mL) is added over about 0.5 hour. The aqueous layer is decanted and the organic phase extracted with two additional portions of acid. The three aqueous extracts are combined, saturated with NaCl and extracted x4 with 50 mL portions of chloroform. The combined chloroform extracts are dried (MgSO$_4$) and concentrated to yield 79.79 g of a brown oil. The product is used without further purification.

Example 36

Preparation of Glycerol-di-(Ethylene glycol methyl ether)

To a suspension of sodium hydride (20.4 g, 0.85 moles) in anhydrous dioxane (500 mL) at cooled to about 10° C. under stream of argon is added ethylene glycol mono-methyl ether (60.92 g, 0.80 moles) over a period of about 1 hour. The mixture is allowed to warm to room temperature and is subsequently refluxed for 1 hour. After warming to room temperature epichlorohydrin (37.0 g, 0.40 moles) is added. The solution is heated over a period of 2 hours until reflux temperature and then refluxing is continued for an additional 48 hours. After cooling, the solvent is removed in vacuo. The resulting solid is slurried in ether (500 mL), cooled to about 10° C. and then 10% HCl (75 mL) is added over about 0.5 hour. The aqueous layer is decanted and the organic phase extracted with two additional portions of acid. The three aqueous extracts are combined, saturated with NaCl and extracted ×4 with 50 mL portions of chloroform. The combined chloroform extracts are dried (MgSO$_4$) and concentrated to yield 59.90 g of a brown oil. The product is used without further purification.

Example 37

Preparation of Glycerol-di-(NEODOL 23-6.5T)

To a suspension of sodium hydride (20.4 g, 0.85 moles) in anhydrous dioxane (500 mL) at cooled to about 10° C. under stream of argon is added NEODOL 23-6.5T (383.2 g, 0.80 moles) over a period of about 1 hour. The mixture is allowed to warm to room temperature and is subsequently refluxed for 1 hour. After warming to room temperature epichlorohydrin (37.0 g, 0.40 moles) is added. The solution is heated over a period of 2 hours until reflux temperature and then refluxing is continued for an additional 48 hours. After cooling, 100 mL of concentrated HCl is added over 1 hour at about 10° C. and the solvent and excess NEODOL 23-6.5T are removed in vacuo. Chromatography over silica gel using THF as eluent yielded 344.7 g of a brown oil. The product is used without further purification.

Example 38

Preparation of Silicon(VI)phthalocyanine-di-Iso PEG 384

A mixture of Silicon(VI)phthalocyanine di-hydroxide (1 g, 1.73 mmoles), glycerol-di-(triethylene glycol methyl ether) (20 g, 52 mmoles) (prepared in accordance with Example 34) and xylenes (175 ml) is slowly heated to reflux over a period of two hours. Once refluxing temperature is achieved, the solution is refluxed an additional 48 hours under a blancket of argon to azeotropically remove the water formed. The solution is cooled to room temperature and the solvent removed under reduced pressure to yield 21.15 g of a blue oil resulted. Q-band $\lambda_{max}$ at 674 nm (water).

Example 39

Preparation of Silicon(VI)naphthalocyanine-di-Iso PEG 384

A mixture of silicon(VI)naphthalocyanine di-hydroxide (1 g, 1.29 mmoles), glycerol-di-(triethylene glycol methyl ether) (15 g, 38.72 mmoles) (prepared in accordance with Example 34) and xylenes (175 ml) is slowly heated to reflux over a period of two hours. Once refluxing temperature is achieved, the solution is refluxed an additional 48 hours under a blancket of argon to azeotropically remove the water formed. The solution is cooled to room temperature and the solvent removed under reduced pressure to yield 16.07 g of a green oil resulted. Q-band $\lambda_{max}$ at 788 nm (water, 1% Triton X-100).

The disinfecting compositions provided in accordance with this invention may be in the form of granules, liquids, bars, and the like, and typically are formulated to provide an in-use pH in the range of 3 to 13, however in the case of non-aqueous or low aqueous compositions the pH ranges may vary outside this range. Various carriers such as sodium sulfate, water, water-ethanol, BPP, MPP, EPP, PPP, sodium carbonate, and the like, may be used routinely to formulate the finished products. Granules may be produced by spray-drying or by agglomeration, using known techniques, to provide products in the density range of 350–950 g/l. Bars may be formulated using conventional extrusion techniques. The photodisinfectant-chelant may be pre-formed, if desired. The compositions may also contain conventional perfumes, bactericides, hydrotropes and the like. In the case of non-aqueous or low aqueous compositions, the cleaning compositions may be applied to an article which is used to deliver the compositions of the present invention to a fabric or to a hard surface. Non-limiting examples of compositions according to this invention are as follows:

| | weight % | | | |
|---|---|---|---|---|
| Ingredients | 40 | 41 | 42 | 43 |
| Sodium LAS | 15 | 30 | 20 | 25 |
| NEODOL | 1 | 1 | 1 | 1 |
| Alkyl Dimethyl Ammonium Chloride | 0.5 | 1 | 0.5 | 0.7 |
| Sodium Tripolyphosphate | 15 | 35 | 22 | 28 |
| Sodium Carbonate | 10 | 10 | 15 | 15 |
| SOKALAN | 2 | 2 | 2 | 2 |
| Carboxymethyl Cellulose | 1 | 1 | 1 | 1 |
| Tinopal CBS-X | 0.1 | 0.1 | 0.1 | 0.1 |
| Soil Release Agent[1] | 0.2 | 0.2 | 0.3 | 0.3 |
| Savinase 6.0T | 0.3 | 0.6 | 0.5 | 0.6 |
| BAN 300T | 0.2 | 0.5 | 0.5 | 0.6 |
| Lipolase 100T | 0.1 | 0.2 | 0.2 | 0.3 |
| CAREZYME 5T | 0.1 | 0.2 | 0.2 | 0.3 |
| Sodium Perborate | — | — | 3.0 | 5.0 |
| NOBS | — | — | 2.0 | 3.0 |
| Photodisinfectant[2] | 0.005 | 0.01 | — | — |
| Photodisinfectant[3] | — | — | 0.008 | 0.01 |
| Moisture + SodiumSulfate + Perfume + Miscellaneous | Balance | Balance | Balance | Balance |

[1]Soil Release Agent according to U.S. Pat. No. 5,415,807 Gosselinnk et al., issued May 16, 1995.
[2]Photodisinfectant according to Example 38.
[3]Photodisinfectant according to Example 39.

Granular disinfectants for textile garments

| | Weight % | | |
|---|---|---|---|
| Ingredients | 44 | 45 | 46 |
| Zeolite | 38 | 35 | 30 |
| Silicate 2.0R | 6 | 4 | 7 |
| Carbonate (sodium) | 9 | 10 | 4 |
| Ethylene diamine tetramethylenphosphonate | 0.2 | 0.1 | 0.3 |
| Brightener 47 | 0.1 | 0.15 | 0.1 |
| Brightener 49 | 0.05 | — | 0.05 |
| Percarbonate | 8 | 5 | 10 |
| NOBS | — | — | 3 |
| TAED | 7 | — | — |
| Savinase (4.0 KNPU/g) | 2 | 1.5 | 2 |
| Lipolase (100000 LU/g) | 0.2 | 0.5 | 0.5 |
| C12–C14 Sulphate | 6 | 6 | 8 |
| C12–C14 AE 4.2 nonionic | 11 | 12 | 10 |
| Soap | 1 | — | — |
| Photodisinfectant[1] | 0.01 | — | — |
| Photodisinfectant[2] | — | 0.1 | — |
| Photodisinfectant[3] | — | — | 0.1 |
| Miscellaneous/Moisture Balance | 100 | 100 | 100 |

[1]Photodisinfectant according to Example 15.
[2]Photodisinfectant according to Example 38.
[3]Photodisinfectant according to Example 31.

Example 47

Disinfectant for treating a textile or situs that is re-activated with a solution

| Ingredient | Weight % |
|---|---|
| Anionic alkyl sulfate | 7 |
| Nonionic surfactant | 5 |
| Zeolite | 10 |
| Trisodium citrate | 2 |
| SKS-6 silicate builder | 10 |
| Acrylate/maleate copolymer | 4 |
| Sodium percarbonate | 25 |
| Sodium carbonate | 5 |
| Ethylenediamine disuccinate | 0.4 |
| Suds suppressor | 2 |
| Enzymes | 1.5 |
| Photodisinfectant[1] | 0.01 |
| Miscellaneous/Moisture Balance | 100 |

[1]Photodisinfectant according to Example 31.

The above embodiment may be allowed to fully dry prior to exposure. After exposure, reactivation with a solution produces more desirable properties.

Example 48

Low aqueous disinfecting composition

| Ingredients | % (wt.) Formula Range |
|---|---|
| Photodisinfectant[1] | 0.005–1.5 |
| BPP[2] | 5–25 |
| 1,2-octanediol | 0.1–7.0 |
| MgAE$_1$S | 0.01–0.8 |
| MgAE$_{4.5}$S | 0.01–0.8 |
| C$_{12}$ Dimethyl Amine Oxide | 0.01–0.8 |
| PEMULEN[3] | 0.05–0.20 |
| perfume | 0.01–1.5 |
| water | balance |
| pH range from about 6 to about 8 | |

[1]Photodisinfectant according to Example 38.
[2]Other co-solvents which can be used herein together with the BPP, MPP, EPP and PPP primary solvents include various glycol ethers, including materials marketed under trademarks such as Carbitol, methyl Carbitol, butyl Carbitol, propyl Carbitol, hexyl Cellosolve, and the like. If desired, and having due regard for safety and odor for in-home use, various conventional chlorinated and hydrocarbon dry cleaning solvents may also be used. Included among these are 1,2-dichloroethane, trichloroethylene, isoparaffins, and mixtures thereof.
[3]As disclosed in U.S. Pat. Nos. 4,758,641 and 5,004,557, such polyacrylates include homopolymers which may be crosslinked to varying degrees, as well as non-crosslinked. Preferred herein are homopolymers having a molecular weight in the range of from about 100,000 to about 10,000,000, preferably 2000,000 to 5,000,000.

Compositions for providing extended disinfectancy to a surface

| Ingredients | Weight % | | | | | |
|---|---|---|---|---|---|---|
| | 49 | 50 | 51 | 52 | 53 | 54 |
| C$_{12}$ alkyl sulphate | 5 | 3 | — | 1 | 1 | 2 |
| nonionic C$_{12}$E$_6$ | 6 | 4 | 8 | 3 | 4 | 3 |
| butyl carbitol | 4 | — | 3 | — | 2 | — |
| sodium carbonate | 8 | 7 | 10 | 30 | | |
| Photobleach[1] | — | 0.01 | — | 0.3 | | |
| Photobleach[2] | 0.1 | — | — | 0.5 | | |

| Ingredients | Weight % | | | | | |
|---|---|---|---|---|---|---|
| | 49 | 50 | 51 | 52 | 53 | 54 |

[1]Photodisinfectant according to Example 15.
[2]Photodisinfectant according to Example 38.
[3]Photodisinfectant according to Example 31.

The composition is applied to a surface which is then wiped clean. The photodisinfectant provides extended anti microbial action.

Compositions to provide swimming pool disinfection

| Ingredients | Weight % | | | |
|---|---|---|---|---|
| | 55 | 56 | 57 | 58 |
| sodium LAS | — | 3 | — | — |
| nonionic C$_{12}$E$_6$ | 2 | 2 | 4 | — |
| C$_{12}$ alkyl sulfate | 4 | — | — | — |
| sodium carbonate | 8 | 7 | 10 | 30 |
| Photobleach[1] | — | 0.01 | — | 0.3 |
| Photobleach[2] | 0.1 | — | — | 0.5 |

[1]Photodisinfectant according to Example 15.
[2]Photodisinfectant according to Example 38.

Fabrics or a situs that are disinfected using the foregoing compositions, typically at usage concentrations of from about 10 ppm to about 10,000 ppm. The surfaces are dried in the presence of light, preferably natural sunlight, to achieve improved photodisinfecting benefits. Once dried, a situs is reactivated by treatment with a solution as defined herein above and the application of light.

What is claimed is:

1. An organosilicon(IV) photosensitizing compound having a Q-band maximum absorption wavelength of 660 nanometers or greater; said organosilicon(IV) photosensitizing compound is a phthalocyanine having the formula:

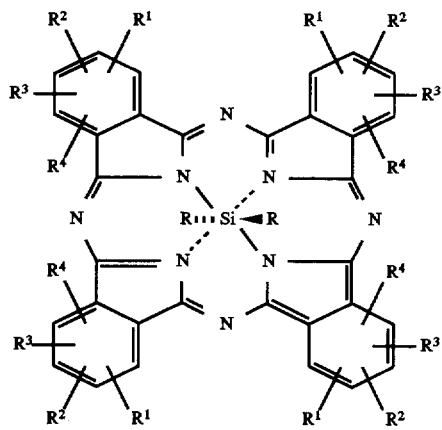

or a naphthalocyanine having the formula:

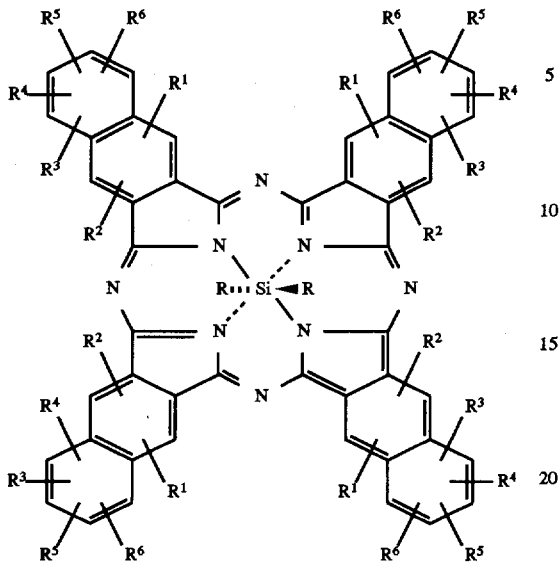

wherein $R^1$, $R^2$, $R^3$, $R^4$, $R^5$, and $R^6$ units are each independently selected from the group consisting of:
a) hydrogen;
b) halogen;
c) hydroxyl;
d) cyano;
e) nitrilo;
f) oximino;
g) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
h) halogen substituted $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
i) polyhydroxyl substituted $C_3$–$C_{22}$ alkyl;
j) $C_1$–$C_{22}$ alkoxy;
k) branched alkoxy having the formula:

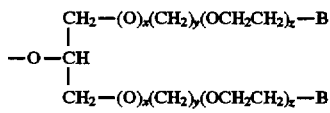

or

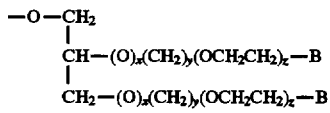

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3{}^{2-}M$, —$OPO_3{}^{2-}M$, and mixtures thereof; M is a water soluble cation in sufficient amount to satisfy charge balance; x is 0 or 1, each y independently has the value from 0 to 6, each z independently has the value from 0 to 100;
l) substituted and unsubstituted aryl;
m) substituted and unsubstituted alkylenearyl;
n) substituted and unsubstituted aryloxy;
o) substituted and unsubstituted oxyalkylenearyl;
p) substituted and unsubstituted alkyleneoxyaryl;
q) $C_1$–$C_{22}$ thioalkyl, $C_4$–$C_{22}$ branched thioalkyl, or mixtures thereof;

r) an ester of the formula —$CO_2R^{10}$ wherein $R^{10}$ comprises
  i) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
  ii) halogen substituted $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
  iii) polyhydroxyl substituted $C_3$–$C_{22}$ alkyl;
  iv) $C_3$–$C_{22}$ glycol;
  v) $C_1$–$C_{22}$ alkoxy;
  vi) $C_4$–$C_{22}$ branched alkoxy;
  vii) substituted and unsubstituted aryl;
  viii) substituted and unsubstituted alkylaryl;
  ix) substituted and unsubstituted aryloxy;
  x) substituted and unsubstituted alkoxyaryl;
  xi) substituted and unsubstituted alkyleneoxyaryl; or mixtures thereof;
s) an alkyleneamino unit of the formula:

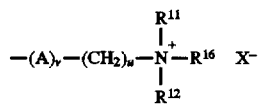

wherein $R^{11}$ and $R^{12}$ comprises $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof; $R^{16}$ comprises:
  i) hydrogen;
  ii) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
  A units comprise nitrogen or oxygen; X comprises chlorine, bromine, iodine, or other water soluble anion, v is 0 or 1, u is from 0 to 22;
t) an amino unit of the formula:

wherein $R^{11}$ and $R^{12}$ comprises $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
u) an alkylethyleneoxy unit of the formula:

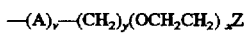

wherein Z comprises:
  i) hydrogen;
  ii) hydroxyl;
  iii) —$CO_2H$;
  iv) —$SO_3$-$M^+$;
  v) —$OSO_3$-$M^+$;
  vi) $C_1$–$C_6$ alkoxy;
  vii) substituted and unsubstituted aryl;
  viii) substituted and unsubstituted aryloxy;
  ix) alkyleneamino; or mixtures thereof;
  A units comprise nitrogen or oxygen, M is a water soluble cation, v is 0 or 1, x is from 0 to 100, y is from 0 to 12;
v) substituted siloxy of the formula:

wherein each $R^7$, $R^8$, and $R^9$ is independently selected from the group consisting of:

i) $C_1-C_{22}$ alkyl, $C_4-C_{22}$ branched alkyl, $C_2-C_{22}$ alkenyl, $C_4-C_{22}$ branched alkenyl, or mixtures thereof;
ii) substituted and unsubstituted aryl;
iii) substituted and unsubstituted aryloxy;
iv) an alkylethyleneoxy unit of the formula:

$$-(A)_v-(CH_2)_y(OCH_2CH_2)_xZ$$

wherein Z comprises:
a) hydrogen;
b) $C_1-C_{30}$ alkyl;
c) hydroxyl;
d) $-CO_2H$;
e) $-SO_3^-M^+$;
f) $-OSO_3^-M^+$;
g) $C_1-C_6$ alkoxy;
h) substituted and unsubstituted aryl;
i) substituted and unsubstituted aryloxy;
j) alkyleneamino; or mixtures thereof;
A units comprise nitrogen or oxygen, M is a water soluble cation, v is 0 or 1, x is from 0 to 100, y is from 0 to 12;

and mixtures thereof; axial R units wherein each R is independently selected from the group consisting of:
a) hydrogen;
b) halogen;
c) hydroxyl;
d) cyano;
e) nitrilo;
f) oximino;
g) $C_1-C_{22}$ alkyl, $C_4-C_{22}$ branched alkyl, $C_2-C_{22}$ alkenyl, $C_4-C_{22}$ branched alkenyl, or mixtures thereof;
h) halogen substituted $C_1-C_{22}$ alkyl, $C_4-C_{22}$ branched alkyl, $C_2-C_{22}$ alkenyl, $C_4-C_{22}$ branched alkenyl, or mixtures thereof;
i) polyhydroxyl substituted $C_3-C_{22}$ alkyl;
j) $C_1-C_{22}$ alkoxy;
k) branched alkoxy having the formula:

$$-O-CH\begin{matrix}CH_2-(O)_x(CH_2)_y(OCH_2CH_2)_z-B\\ \\ CH_2-(O)_x(CH_2)_y(OCH_2CH_2)_z-B\end{matrix}$$

or $$-O-CH_2\\ |\\ CH-(O)_x(CH_2)_y(OCH_2CH_2)_z-B\\ |\\ CH_2-(O)_x(CH_2)_y(OCH_2CH_2)_z-B$$

wherein B is hydrogen, hydroxyl, $C_1-C_{30}$ alkyl, $C_1-C_{30}$ alkoxy, $-CO_2H$, $-CH_2CO_2H$, $-SO_3^-M^+$, $-OSO_3^-M^+$, $-PO_3^{2-}M$, $-OPO_3^{2-}M$, and mixtures thereof; M is a water soluble cation in sufficient amount to satisfy charge balance; x is 0 or 1, each y independently has the value from 0 to 6, each z independently has the value from 0 to 100;

l) substituted and unsubstituted aryl;
m) substituted and unsubstituted alkylenearyl;
n) substituted and unsubstituted aryloxy;
o) substituted and unsubstituted oxyalkylenearyl;
p) substituted and unsubstituted alkyleneoxyaryl;

q) $C_1-C_{22}$ thioalkyl, $C_4-C_{22}$ branched thioalkyl, or mixtures thereof;
r) an alkyleneamino unit of the formula:

$$-(A)_v-(CH_2)_u-\underset{R^{12}}{\overset{R^{11}}{\underset{|}{\overset{|}{N^+}}}}-R^{16}\quad X^-$$

wherein $R^{11}$ and $R^{12}$ comprises $C_1-C_{22}$ alkyl, $C_4-C_{22}$ branched alkyl, $C_2-C_{22}$ alkenyl, $C_4-C_{22}$ branched alkenyl, or mixtures thereof; $R^{16}$ comprises:
i) hydrogen;
ii) $C_1-C_{22}$ alkyl, $C_4-C_{22}$ branched alkyl, $C_2-C_{22}$ alkenyl, $C_4-C_{22}$ branched alkenyl, or mixtures thereof;

A units comprise nitrogen or oxygen; X comprises chlorine, bromine, iodine, or other water soluble anion, v is 0 or 1, u is from 0 to 22;

s) an amino unit of the formula:

$$-NR^{11}R^{12}$$

wherein $R^{11}$ and $R^{12}$ comprises $C_1-C_{22}$ alkyl, $C_4-C_{22}$ branched alkyl, $C_2-C_{22}$ alkenyl, $C_4-C_{22}$ branched alkenyl, or mixtures thereof;

t) an alkylethyleneoxy unit of the formula:

$$-(A)_v-(CH_2)_y(OCH_2CH_2)_xZ$$

wherein Z comprises:
i) hydrogen;
ii) hydroxyl;
iii) $-CO_2H$;
iv) $-SO_3^-M^+$;
v) $-OSO_3^-M^+$;
vi) $C_1-C_6$ alkoxy;
vii) substituted and unsubstituted aryl;
viii) substituted and unsubstituted aryloxy;
ix) alkyleneamino; or mixtures thereof;

A comprises nitrogen or oxygen, M is a water soluble cation, v is 0 or 1, x is from 0 to 100, y is from 0 to 12;

u) carboxylate of the formula:

$$-O-\overset{O}{\underset{}{\overset{\|}{C}}}-R^{10}$$

wherein $R^{10}$ comprises:
i) $C_1-C_{22}$ alkyl, $C_4-C_{22}$ branched alkyl, $C_2-C_{22}$ alkenyl, $C_4-C_{22}$ branched alkenyl, or mixtures thereof;
ii) halogen substituted $C_1-C_{22}$ alkyl, $C_4-C_{22}$ branched alkyl, $C_2-C_{22}$ alkenyl, $C_4-C_{22}$ branched alkenyl, or mixtures thereof;
iii) poly-hydroxyl substituted $C_3-C_{22}$ alkyl;
iv) $C_3-C_{22}$ glycol;
v) $C_1-C_{22}$ alkoxy;
vi) $C_4-C_{22}$ branched alkoxy;
vii) substituted and unsubstituted aryl;
viii) substituted and unsubstituted alkylaryl;
ix) substituted and unsubstituted aryloxy;
x) substituted and unsubstituted alkoxyaryl;
xi) substituted and unsubstituted alkyleneoxyaryl;
xii) alkyleneamino; or mixtures thereof;

v) substituted siloxy of the formula:

$$-OSiR^7R^8R^9$$

wherein each $R^7$, $R^8$, and $R^9$ is independently selected from the group consisting of:
i) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
ii) substituted and unsubstituted aryl;
iii) substituted and unsubstituted aryloxy;
iv) an alkylethyleneoxy unit of the formula:

$$-(A)_v-(CH_2)_y(OCH_2CH_2)_zZ$$

wherein Z comprises:
a) hydrogen;
b) $C_1$–$C_{30}$ alkyl,
c) hydroxyl;
d) $-CO_2H$;
e) $-SO_3$-$M^+$;
f) $-OSO_3$-$M^+$;
g) $C_1$–$C_6$ alkoxy;
h) substituted and unsubstituted aryl;
i) substituted and unsubstituted aryloxy;
j) alkyleneamino; or mixtures thereof;
A units comprise nitrogen or oxygen, M is a water soluble cation, v is 0 or 1, x is from 0 to 100, y is from 0 to 12;
and mixtures thereof.

2. A composition according to claim 1 wherein the organosilicon photosensitizing compound comprises $R^1$, $R^2$, $R^3$, $R^4$, $R^5$, and $R^6$ units independently selected from the group consisting of hydrogen, hydroxyl, halogen, $C_1$–$C_{22}$ thioalkyl, $C_4$–$C_{22}$ branched thioalkyl, $C_1$–$C_{22}$ alkoxy, $C_1$–$C_{22}$ branched alkoxy, aryloxy, an alkylethyleneoxy unit of the formula $$-(A)_v-(CH_2)_y(OCH_2CH_2)_zZ$$

wherein Z comprises hydrogen, hydroxyl, $-CO_2H$, $-SO_3$-$M^+$, $-OSO_3$-$M^+$, $C_1$–$C_6$ alkoxy, substituted and unsubstituted aryl, substituted and unsubstituted aryloxy, alkyleneamino; and mixtures thereof; A comprises nitrogen or oxygen, M is a water soluble cation, v is 0 or 1, x is from 0 to 100, y is from 0 to 12.

3. A composition according to claim 2 wherein axial R units comprise:
a) alkylethyleneoxy units of the formula $$-(A)_v-(CH_2)_y(OCH_2CH_2)_zZ$$

wherein Z comprises hydrogen, hydroxyl, $-CO_2H$, $-SO_3$-$M^+$, $-OSO_3$-$M^+$, $C_1$–$C_6$ alkoxy, substituted and unsubstituted aryl, substituted and unsubstituted aryloxy, alkyleneamino; A comprises nitrogen or oxygen, M is a water soluble cation, v is 0 or 1, x is from 0 to 100, y is from 0 to 12;

b) branched alkoxy having the formula $$-O-\underset{\underset{CH_2-(O)_x(CH_2)_y(OCH_2CH_2)_z-B}{|}}{\overset{CH_2-(O)_x(CH_2)_y(OCH_2CH_2)_z-B}{|}}{CH}$$

or $$-O-CH_2-\underset{\underset{CH_2-(O)_x(CH_2)_y(OCH_2CH_2)_z-B}{|}}{\overset{}{|}}{CH}-(O)_x(CH_2)_y(OCH_2CH_2)_z-B$$

wherein B is hydrogen, hydroxyl, $C_1$–$C_{30}$ alkyl, $C_1$–$C_{30}$ alkoxy, $-CO_2H$, $-CH_2CO_2H$, $-SO_3$-$M^+$, $-OSO_3$-$M^+$, $-PO_3^{2-}M$, $-OPO_3^{2-}M$, and mixtures thereof; M is a water soluble cation in sufficient amount to satisfy charge balance; x is 0 or 1, each y independently has the value from 0 to 6, each z independently has the value from 0 to 100;

c) substituted siloxy of the formula $$-OSiR^7R^8R^9$$

wherein each $R^7$, $R^8$, and $R^9$ is independently selected from the group consisting of $C_1$–$C_{22}$ alkyl, $C_4$–$C_{22}$ branched alkyl, $C_1$–$C_{22}$ alkenyl, $C_4$–$C_{22}$ branched alkenyl, substituted and unsubstituted aryl, substituted and unsubstituted aryloxy, an alkylethyleneoxy unit of the formula $$-(A)_v-(CH_2)_y(OCH_2CH_2)_zZ$$

wherein Z comprises hydrogen, $C_1$–$C_{30}$ alkyl, hydroxyl, $-CO_2H$, $-SO_3$-$M^+$, $-OSO_3$-$M^+$, $C_1$–$C_6$ alkoxy, substituted and unsubstituted aryl, substituted and unsubstituted aryloxy, alkyleneamino, and mixtures thereof; A units comprise nitrogen or oxygen, M is a water soluble cation, v is 0 or 1, x is from 0 to 100, y is from 0 to 12; and d) mixtures thereof.

4. A composition according to claim 3 wherein the organosilicon photosensitizing unit is phthalocyanine and the axial R unit is a branched alkoxy having the formula $$-O-\underset{\underset{CH_2-(O)_x(CH_2)_y(OCH_2CH_2)_z-B}{|}}{\overset{CH_2-(O)_x(CH_2)_y(OCH_2CH_2)_z-B}{|}}{CH}$$

or $$-O-CH_2-\underset{\underset{CH_2-(O)_x(CH_2)_y(OCH_2CH_2)_z-B}{|}}{\overset{}{|}}{CH}-(O)_x(CH_2)_y(OCH_2CH_2)_z-B$$

wherein B is hydrogen, hydroxyl, $C_1$–$C_{30}$ alkyl, $C_1$–$C_{30}$ alkoxy, $-CO_2H$, $-CH_2CO_2H$, $-SO_3$-$M^+$, $-OSO_3$-$M^+$, $-PO_3^{2-}M$, and mixtures thereof; M is a water soluble cation in sufficient mount to satisfy charge balance; x is 0 or 1, each y independently has the value from 0 to 6, each z independently has the value from 0 to 100.

5. A composition according to claim 4 wherein the organosilicon photosensitizing compound comprises one or more $R^1$, $R^2$, $R^3$ and $R^4$ unit wherein each unit is independently selected from the group consisting of halogen, $C_1$–$C_{22}$ thioalkyl, $C_4$–$C_{22}$ branched thioalkyl, $C_1$–$C_{22}$ alkoxy, $C_1$–$C_{22}$ branched alkoxy, and mixtures thereof.

6. A composition according to claim 5 wherein the organosilicon photosensitizing compound comprises one or more $R^1$, $R^2$, $R^3$ and $R^4$ unit wherein each unit is independently halogen or $C_1$–$C_6$ alkoxy.

7. A composition according to claim 6 wherein the organosilicon photosensitizing compound comprises one or more $R^1$, $R^2$, $R^3$; and $R^4$ unit wherein each unit is methoxy.

8. A composition according to claim 3 wherein the organosilicon photosensitizing compound comprises a substituted or unsubstituted naphthalocyanine moiety.

9. A composition according to claim 8 wherein the organosilicon photosensitizing compound comprises one or more $R^1$, $R^2$, $R^3$, $R^4$, $R^5$ and $R^6$ unit wherein each unit is independently selected from the group consisting of halogen, $C_1$–$C_{22}$ thioalkyl, $C_4$–$C_{22}$ branched thioalkyl, $C_1$–$C_{22}$ alkoxy, $C_1$–$C_{22}$ branched alkoxy, and mixtures thereof.

10. A composition according to claim 9 wherein the organosilicon photosensitizing compound comprises one or more $R^1$, $R^2$, $R^3$, $R^4$, $R^5$ and $R^6$ unit wherein each unit is independently chlorine, bromine, or iodine.

11. A composition according to claim 10 wherein the organosilicon photosensitizing compound comprises one or more $R^1$, $R^2$, $R^3$, $R^4$, $R^5$ and $R^6$ unit wherein each unit is chlorine or bromine.

12. A composition according to claim 1 wherein the adjunct ingredients are members selected from the group consisting of buffers, builders, chelants, filler salts, soil release agents dispersants, enzymes, enzyme boosters, perfumes, thickeners, solvents, clays, bleaches, and mixtures thereof.

13. A composition according to claim 1 comprising from about 0.005 to about 2000 ppm organosilicon photodisinfecting compound.

14. A composition according to claim 1 comprising from about 0.1 to about 1000 ppm organosilicon photodisinfecting compound.

15. A silicon phthalocyanine or silicon naphthalocyanine photodisinfecting composition comprising:

a) a silicon(IV) phthalocyanine of the formula:

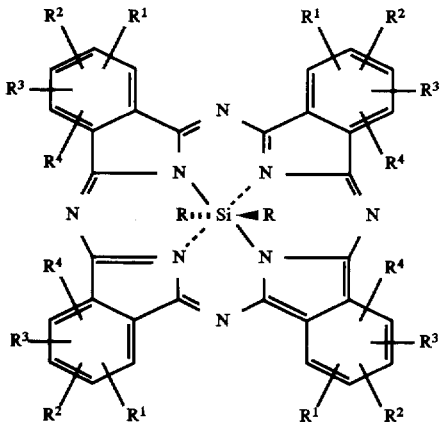

or a silicon(IV) naphthalocyanine of the formula:

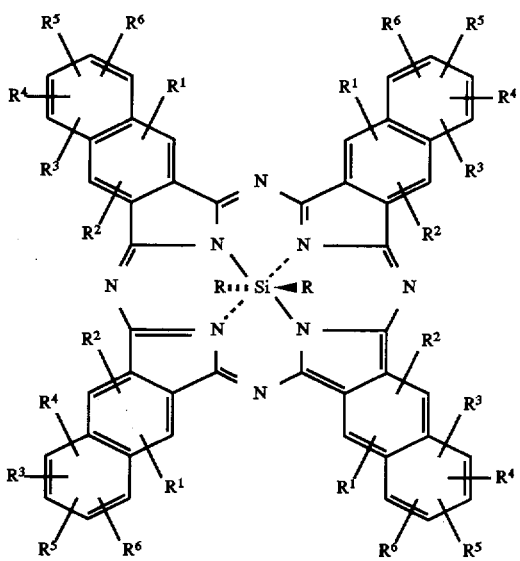

wherein $R^1$, $R^2$, $R^3$, $R^4$, $R^5$, and $R^6$ units are moieties that provide a positive red shift value of at least 1 when said moieties are substituted for hydrogen; wherein the R units are axial units, said R units independently selected from the group consisting of:

a) hydrogen;

b) halogen;

c) hydroxyl;

d) cyano;

e) nitrilo;

f) oximino;

g) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;

h) halogen substituted $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;

i) polyhydroxyl substituted $C_3$–$C_{22}$ alkyl;

j) $C_1$–$C_{22}$ alkoxy;

k) branched alkoxy having the formula:

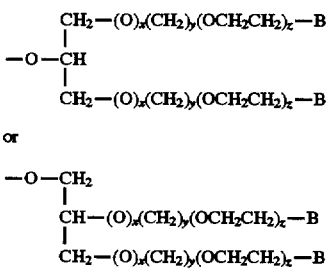

wherein B is hydrogen, hydroxyl, $C_1$–$C_{30}$ alkyl, $C_1$–$C_{30}$ alkoxy, $-CO_2H$, $-CH_2CO_2H$, $-SO_3$-$M^+$, $-OSO_3$-$M^+$, $-PO_3^{2-}M$, $-OPO_3^{2-}M$, and mixtures thereof; M is a water soluble cation in sufficient amount to satisfy charge balance; x is 0 or 1, each y independently has the value from 0 to 6, each z independently has the value from 0 to 100;

l) substituted and unsubstituted aryl;

m) substituted and unsubstituted alkylenearyl;

n) substituted and unsubstituted aryloxy;

o) substituted and unsubstituted oxyalkylenearyl;

p) substituted and unsubstituted alkyleneoxyaryl;

q) $C_1$–$C_{22}$ thioalkyl, $C_4$–$C_{22}$ branched thioalkyl, or mixtures thereof;

r) an alkyleneamino unit of the formula:

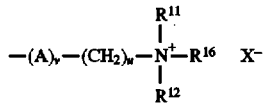

wherein $R^{11}$ and $R^{12}$ comprises $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof; $R^{16}$ comprises:
  i) hydrogen;
  ii) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;

A units comprise nitrogen or oxygen; X comprises chlorine, bromine, iodine, or other water soluble anion, v is 0 or 1, u is from 0 to 22;

s) an amino unit of the formula:

wherein $R^{11}$ and $R^{12}$ comprises $C_1$–$C_{22}$ alkyl, $C_4$–$C_{22}$ branched alkyl, $C_2$–$C_{22}$ alkenyl, $C_4$–$C22$ branched alkenyl, or mixtures thereof;

t) an alkylethyleneoxy unit of the formula:

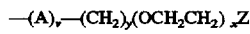

wherein Z comprises:
  i) hydrogen;
  ii) hydroxyl;
  iii) —$CO_2H$;
  iv) —$SO_3$-$M^+$;
  v) —$OSO_3$-$M^+$;
  vi) $C_1$–$C_6$ alkoxy;
  vii) substituted and unsubstituted aryl;
  viii) substituted and unsubstituted aryloxy;
  ix) alkyleneamino; or mixtures thereof;
  A comprises nitrogen or oxygen, M is a water soluble cation, v is 0 or 1, x is from 0 to 100, y is from 0 to 12;

u) carboxylate of the formula:

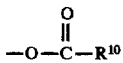

wherein $R^{10}$ comprises:
  i) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
  ii) halogen substituted $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
  iii) poly-hydroxyl substituted $C_3$–$C_{22}$ alkyl;
  iv) $C_3$–$C_{22}$ glycol;
  v) $C_1$–$C_{22}$ alkoxy;
  vi) $C_4$–$C_{22}$ branched alkoxy;
  vii) substituted and unsubstituted aryl;
  viii) substituted and unsubstituted alkylaryl;
  ix) substituted and unsubstituted aryloxy;

x) substituted and unsubstituted alkoxyaryl;

xi) substituted and unsubstituted alkyleneoxyaryl;

xii) alkyleneamino; or mixtures thereof;

v) substituted siloxy of the formula:

wherein each $R^7$, $R^8$, and $R^9$ is independently selected from the group consisting of:
  i) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
  ii) substituted and unsubstituted aryl;
  iii) substituted and unsubstituted aryloxy;
  iv) an alkylethyleneoxy unit of the formula:

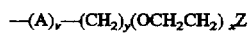

wherein Z comprises:
  a) hydrogen;
  b) $C_1$–$C_{30}$ alkyl,
  c) hydroxyl;
  d) —$CO_2H$;
  e) —$SO_3$-$M^+$;
  f) —$OSO_3$-$M^+$;
  g) $C_1$–$C_6$ alkoxy;
  h) substituted and unsubstituted aryl;
  i) substituted and unsubstituted aryloxy;
  j) alkyleneamino; or mixtures thereof;
  A units comprise nitrogen or oxygen, M is a water soluble cation, v is 0 or 1, x is from 0 to 100, y is from 0 to 12;
and mixtures thereof; and b) the balance adjunct ingredients.

16. A composition according to claim 15 wherein the positive red shift value is at least 10.

17. A composition according to claim 15 wherein the positive red shift value is at least 30.

18. A composition according to claim 15 wherein the organosilicon photosensitizing compound comprises $R^1$, $R^2$, $R^3$, $R^4$, $R^5$, and $R^6$ units independently selected from the group consisting of hydrogen, hydroxyl, halogen, $C_1$–$C_{22}$ thioalkyl, $C_4$–$C_{22}$ branched thioalkyl, $C_1$–$C_{22}$ alkoxy, $C_1$–$C_{22}$ branched alkoxy, aryloxy, an alkylethyleneoxy unit of the formula

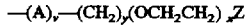

wherein Z comprises hydrogen, hydroxyl, —$CO_2H$, —$SO_3$-$M^+$, —$OSO_3$-$M^+$, $C_1$–$C_6$ alkoxy, substituted and unsubstituted aryl, substituted and unsubstituted aryloxy, alkyleneamino; and mixtures thereof; A comprises nitrogen or oxygen, M is a water soluble cation, v is 0 or 1, x is from 0 to 100, y is from 0 to 12.

19. A composition according to claim 18 wherein the organosilicon photosensitizing compound comprises R units independently selected from the group consisting of alkylethyleneoxy units of the formula

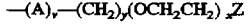

wherein Z comprises hydrogen, hydroxyl, —$CO_2H$, —$SO_3$-$M^+$, —$OSO_3$-$M^+$, $C_1$–$C_6$ alkoxy, substituted and unsubstituted aryl, substituted and unsubstituted aryloxy, alkyleneamino; and mixtures thereof; A comprises nitrogen or oxygen, M is a water soluble cation, v is 0 or 1, x is from 0 to 100, y is from 0 to 12; branched alkoxy having the formula

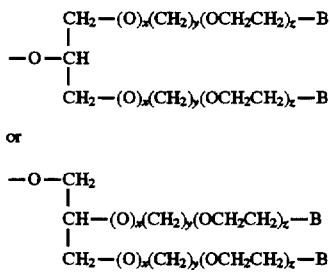

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, each z independently has the value from 0 to 100; substituted siloxy of the formula

wherein each $R^7$, $R^8$, and $R^9$ is independently selected from the group consisting of $C_1$–$C_{22}$ alkyl, $C_4$–$C_{22}$ branched alkyl, $C_1$–$C_{22}$ alkenyl, $C_4$–$C_{22}$ branched alkenyl, and mixtures thereof; substituted and unsubstituted aryl; substituted and unsubstituted aryloxy; an alkylethyleneoxy unit of the formula

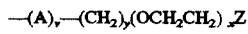

wherein Z comprises hydrogen, $C_1$–$C_{30}$ alkyl, hydroxyl, —$CO_2H$, —$SO_3$-$M^+$, —$OSO_3$-$M^+$, $C_1$–$C_6$ alkoxy, substituted and unsubstituted aryl, substituted and unsubstituted aryloxy, alkyleneamino; and mixtures thereof; A units comprise nitrogen or oxygen, M is a water soluble cation, v is 0 or 1, x is from 0 to 100, y is from 0 to 12; and mixtures thereof.

20. A composition according to claim 19 wherein $R^1$, $R^2$, $R^3$, $R^4$, $R^5$, and $R^6$ is independently selected from the group consisting of halogen, $C_1$–$C_{22}$ thioalkyl, $C_4$–$C_{22}$ branched thioalkyl, $C_1$–$C_{22}$ alkoxy, $C_1$–$C_{22}$ branched alkoxy, aryloxy, and mixtures thereof.

21. A composition according to claim 20 wherein $R^1$, $R^2$, $R^3$, $R^4$, $R^5$, and $R^6$ is independently selected from the group consisting of halogen, $C_1$–$C_{22}$ alkoxy, and mixtures thereof.

22. A composition according to claim 20 wherein the photobleaching composition comprises a silicon phthalocyanine.

23. A composition according to claim 22 wherein $R^1$, $R^2$, $R^3$, $R^4$, $R^5$, and $R^6$ is independently selected from the group consisting of halogen, $C_1$–$C_6$ alkoxy, and mixtures thereof.

24. A composition according to claim 23 wherein $R^1$, $R^2$, $R^3$, $R^4$, $R^5$, and $R^6$ is methoxy.

25. A composition according to claim 21 wherein the photobleaching composition comprises a silicon naphthalocyanine.

26. A composition according to claim 25 wherein $R^1$, $R^2$, $R^3$, $R^4$, $R^5$, and $R^6$ is independently selected from the group consisting of halogen, $C_1$–$C_6$ alkoxy, and mixtures thereof.

27. A composition according to claim 26 wherein $R^1$, $R^2$, $R^3$, $R^4$, $R^5$, and $R^6$ is independently selected from the group consisting of chlorine, bromine, iodine and mixtures thereof.

28. A composition according to claim 27 wherein $R^1$, $R^2$, $R^3$, $R^4$, $R^5$, and $R^6$ is chlorine or bromine.

29. A composition according to claim 15 wherein the adjunct ingredients are selected from the group consisting of detersive surfactants, buffers, builders, chelants, filler salts, soil release agents, dispersants, enzymes, enzyme boosters, perfumes, thickeners, clays, bleaches, solvents, and mixtures thereof.

30. A composition according to claim 29 wherein the adjunct ingredients are selected from the group consisting of solvents, chelants, nonionic surfactants and mixtures thereof.

31. A silicon phthalocyanine or silicon naphthalocyanine photodisinfecting composition comprising:

a) a silicon(IV) phthalocyanine of the formula:

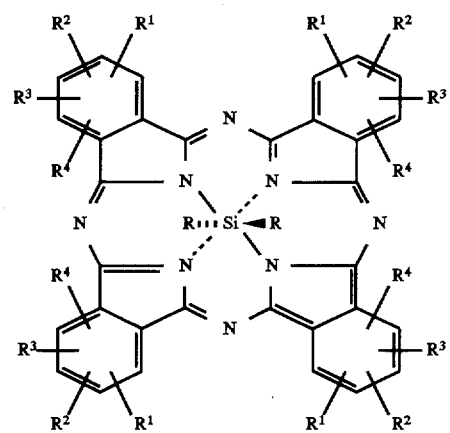

or a silicon(IV) naphthalocyanine of the formula:

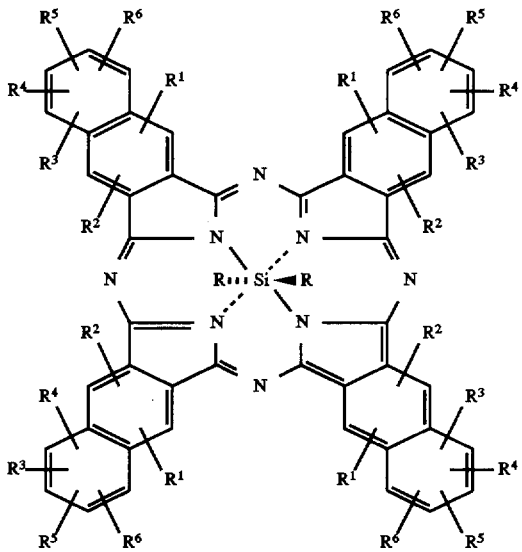

wherein $R^1$, $R^2$, $R^3$, $R^4$, $R^5$, and $R^6$ units are moieties that provide a positive $\Delta_{triplet}$ yield when said moiety replaces hydrogen;

wherein the R units are axial units, said R units independently selected from the group consisting of:

a) hydrogen;
b) halogen;
c) hydroxyl;
d) cyano;

e) nitrilo;

f) oximino;

g) $C_1-C_{22}$ alkyl, $C_4-C_{22}$ branched alkyl, $C_2-C_{22}$ alkenyl, $C_4-C_{22}$ branched alkenyl, or mixtures thereof;

h) halogen substituted $C_1-C_{22}$ alkyl, $C_4-C_{22}$ branched alkyl, $C_2-C_{22}$ alkenyl, $C_4-C_{22}$ branched alkenyl, or mixtures thereof;

i) polyhydroxyl substituted $C_3-C_{22}$ alkyl;

j) $C_1-C_{22}$ alkoxy;

k) branched alkoxy having the formula:

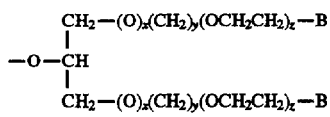

or

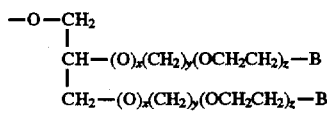

wherein B is hydrogen, hydroxyl, $C_1-C_{30}$ alkyl, $C_1-C_{30}$ alkoxy, $-CO_2H$, $-CH_2CO_2H$, $-SO_3\text{-}M^+$, $-OSO_3\text{-}M^+$, $-PO_3^{2-}M$, $-OPO_3^{2-}M$, and mixtures thereof; M is a water soluble cation in sufficient amount to satisfy charge balance; x is 0 or 1, each y independently has the value from 0 to 6, each z independently has the value from 0 to 100;

l) substituted and unsubstituted aryl;

m) substituted and unsubstituted alkylenearyl;

n) substituted and unsubstituted aryloxy;

o) substituted and unsubstituted oxyalkylenearyl;

p) substituted and unsubstituted alkyleneoxyaryl;

q) $C_1-C_{22}$ thioalkyl, $C_4-C_{22}$ branched thioalkyl, or mixtures thereof;

r) an alkyleneamino unit of the formula:

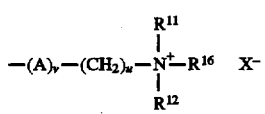

wherein $R^{11}$ and $R^{12}$ comprises $C_1-C_{22}$ alkyl, $C_4-C_{22}$ branched alkyl, $C_2-C_{22}$ alkenyl, $C_4-C_{22}$ branched alkenyl, or mixtures thereof; $R^{16}$ comprises:

i) hydrogen;

ii) $C_1-C_{22}$ alkyl, $C_4-C_{22}$ branched alkyl, $C_2-C_{22}$ alkenyl, $C_4-C_{22}$ branched alkenyl, or mixtures thereof;

A units comprise nitrogen or oxygen; X comprises chlorine, bromine, iodine, or other water soluble anion, v is 0 or 1, u is from 0 to 22;

s) an amino unit of the formula:

wherein $R^{11}$ and $R^{12}$ comprises $C_1-C_{22}$ alkyl, $C_4-C_{22}$ branched alkyl, $C_2-C_{22}$ alkenyl, $C_4-C_{22}$ branched alkenyl, or mixtures thereof;

t) an alkylethyleneoxy unit of the formula:

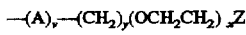

wherein Z comprises:

i) hydrogen;

ii) hydroxyl;

iii) $-CO_2H$;

iv) $-SO_3\text{-}M^+$;

v) $-OSO_3\text{-}M^+$;

vi) $C_1-C_6$ alkoxy;

vii) substituted and unsubstituted aryl;

viii) substituted and unsubstituted aryloxy;

ix) alkyleneamino; or mixtures thereof;

A comprises nitrogen or oxygen, M is a water soluble cation, v is 0 or 1, x is from 0 to 100, y is from 0 to 12;

u) carboxylate of the formula:

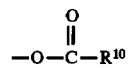

wherein $R^{10}$ comprises:

i) $C_1-C_{22}$ alkyl, $C_4-C_{22}$ branched alkyl, $C_2-C_{22}$ alkenyl, $C_4-C_{22}$ branched alkenyl, or mixtures thereof;

ii) halogen substituted $C_1-C_{22}$ alkyl, $C_4-C_{22}$ branched alkyl, $C_2-C_{22}$ alkenyl, $C_4-C_{22}$ branched alkenyl, or mixtures thereof;

iii) poly-hydroxyl substituted $C_3-C_{22}$ alkyl;

iv) $C_3-C_{22}$ glycol;

v) $C_1-C_{22}$ alkoxy;

vi) $C_4-C_{22}$ branched alkoxy;

vii) substituted and unsubstituted aryl;

viii) substituted and unsubstituted alkylaryl;

ix) substituted and unsubstituted aryloxy;

x) substituted and unsubstituted alkoxyaryl;

xi) substituted and unsubstituted alkyleneoxyaryl;

xii) alkyleneamino; or mixtures thereof;

v) substituted siloxy of the formula:

wherein each $R^7$, $R^8$, and $R^9$ is independently selected from the group consisting of:

i) $C_1-C_{22}$ alkyl, $C_4-C_{22}$ branched alkyl, $C_2-C_{22}$ alkenyl, $C_4-C_{22}$ branched alkenyl, or mixtures thereof;

ii) substituted and unsubstituted aryl;

iii) substituted and unsubstituted aryloxy;

iv) an alkylethyleneoxy unit of the formula:

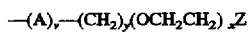

wherein Z comprises:

a) hydrogen;

b) $C_1-C_{30}$ alkyl, c) hydroxyl;

d) $-CO_2H$;

e) $-SO_3\text{-}M^+$;

f) $-OSO_3\text{-}M^+$;

g) $C_1-C_6$ alkoxy;

h) substituted and unsubstituted aryl;

i) substituted and unsubstituted aryloxy;

j) alkyleneamino; or mixtures thereof;

A units comprise nitrogen or oxygen, M is a water soluble cation, v is 0 or 1, x is from 0 to 100, y is from 0 to 12;

and mixtures thereof; and b) the balance adjunct ingredients.

32. A composition according to claim 31 wherein the $\Delta_{max}$ yield is greater than 10.

33. A composition according to claim 31 wherein the $\Delta_{max}$ yield is greater than 30.

34. An organosilicon(IV) photosensitizing compound having a Q-band maximum absorption wavelength of 660 nanometers or greater said organosilicon(IV) photosensitizing compound is a phthalocyanine having the formula

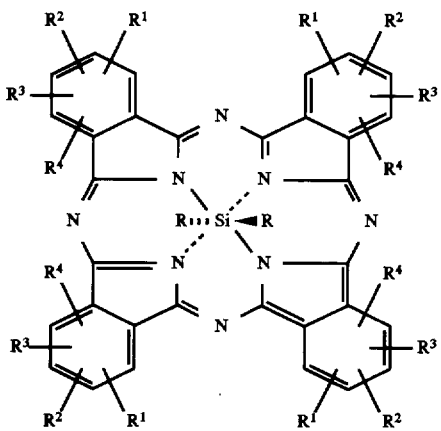

or a naphthalocyanine having the formula:

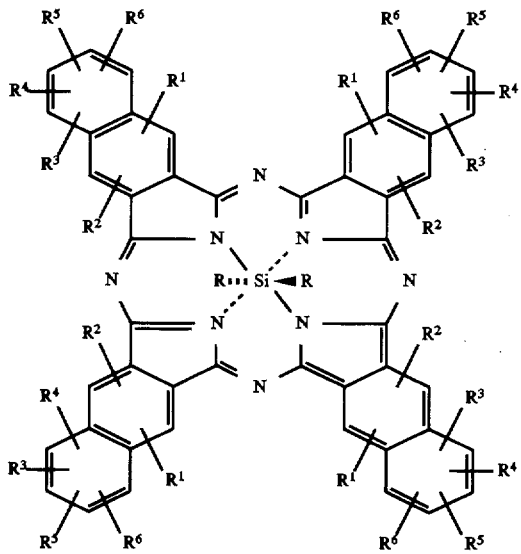

wherein $R^1$, $R^2$, $R^3$, $R^4$, $R^5$, and $R^6$ units are each independently selected from the group consisting of:

a) hydrogen;
b) halogen;
c) hydroxyl;
d) cyano;
e) nitrilo;
f) oximino;
g) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;
h) halogen substituted $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

i) polyhydroxyl substituted $C_3$–$C_{22}$ alkyl;
j) $C_1$–$C_{22}$ alkoxy;
k) branched alkoxy having the formula

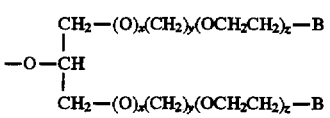

or

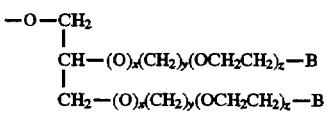

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3^{2-}M$, —$OPO_3^{2-}M$, or mixtures thereof; M is a water soluble cation in sufficient mount to satiny charge balance; x is 0 or 1, each y independently has the value from 0 to 6, each z independently has the value from 0 to 100;

l) substituted aryl, unsubstituted aryl, or mixtures thereof;
m) substituted alkylenearyl, unsubstituted alkylenearyl, or mixtures thereof;
n) substituted aryloxy, unsubstituted aryloxy, or mixtures thereof;
o) substituted oxyalkylenearyl, unsubstituted oxyalkylenearyl, or mixtures thereof;
p) substituted alkyleneoxyaryl, unsubstituted alkyleneoxyaryl, or mixtures thereof;
q) $C_1$–$C_{22}$ thioalkyl, $C_3$–$C_{22}$ branched thioalkyl, or mixtures thereof;
r) an ester of the formula —$CO_2R^{10}$ wherein $R^{10}$ is
   i) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;
   ii) halogen substituted $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;
   iii) polyhydroxyl substituted $C_3$–$C_{22}$ alkyl;
   iv) $C_3$–$C_{22}$ glycol;
   v) $C_1$–$C_{22}$ alkoxy;
   vi) $C_3$–$C_{22}$ branched alkoxy;
   vii) substituted aryl, unsubstituted aryl, or mixtures thereof;
   viii) substituted alkylenearyl, unsubstituted alkylenearyl, or mixtures thereof;
   ix) substituted aryloxy, unsubstituted aryloxy, or mixtures thereof;
   x) substituted oxyalkylenearyl, unsubstituted oxyalkylenearyl, or mixtures thereof;
   xi) substituted alkyleneoxyaryl, unsubstituted alkyleneoxyaryl, or mixtures thereof;
s) an alkyleneamino unit of the formula

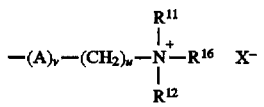

wherein $R^{11}$ and $R^{12}$ is $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof; $R^{16}$ is:
   i) hydrogen;
   ii) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

A units comprise nitrogen or oxygen; X is a water soluble anion; v is 0 or 1, u is from 1 to 22;

t) an amino unit of the formula

wherein $R^{11}$ and $R^{12}$ is $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

u) an alkylethyleneoxy unit of the formula

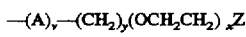

wherein Z is:
  i) hydrogen;
  ii) hydroxyl;
  iii) —$CO_2H$;
  iv) —$SO_3$-$M^+$;
  v) —$OSO_3$-$M^+$;
  vi) $C_1$–$C_6$ alkoxy;
  vii) substituted aryl, unsubstituted aryl, or mixtures thereof;
  viii) substituted aryloxy, unsubstituted aryloxy, or mixtures thereof;
  alkyleneamino; or mixtures thereof;
  A is nitrogen or oxygen, M is a water soluble cation, v is 0 or 1, x is from 0 to 100, y is from 0 to 12;

v) substituted siloxy of the formula

wherein each $R^7$, $R^8$, and $R^9$ is independently:
  i) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;
  ii) substituted aryl, unsubstituted aryl, or mixtures thereof;
  iii) substituted aryloxy, unsubstituted aryloxy, or mixtures thereof;
  iv) an alkylethyleneoxy unit of the formula

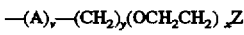

wherein Z is:
  a) hydrogen;
  b) $C_1$–$C_{30}$ alkyl,
  c) hydroxyl;
  d) —$CO_2H$;
  e) —$SO_3$-$M^+$;
  f) —$OSO_3$-$M^+$;
  g) $C_1$–$C_6$ linear alkoxy, $C_3$–$C_6$ branched alkoxy, or mixtures thereof;
  h) substituted aryl, unsubstituted aryl, or mixtures thereof;
  i) substituted aryloxy, unsubstituted aryloxy, or mixtures thereof;
  j) alkyleneamino; or mixtures thereof;
  A is nitrogen or oxygen, M is a water soluble cation, v is 0 or 1, x is from 0 to 100, y is from 0 to 12; or mixtures thereof; and mixtures thereof; and wherein the R units are axial units, said R units independently selected from the group consisting of:

a) hydrogen;
b) halogen;
c) hydroxyl;
d) cyano;
e) nitrilo;
f) oximino;
g) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;
h) halogen substituted $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;
i) polyhydroxyl substituted $C_3$–$C_{22}$ alkyl;
j) $C_1$–$C_{22}$ alkoxy;
k) branched alkoxy having the formula

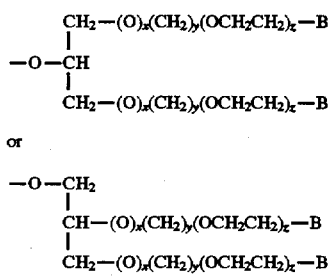

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3^{2-}M$, —$OPO_3^{2-}M$, or mixtures thereof; M is a water soluble cation; x is 0 or 1, each y independently has the value from 0 to 6, each z independently has the value from 0 to 100;

l) substituted aryl, unsubstituted aryl, or mixtures thereof;
m) substituted alkylenearyl, unsubstituted alkylenearyl, or mixtures thereof;
n) substituted aryloxy, unsubstituted aryloxy, or mixtures thereof;
o) substituted oxyalkylenearyl, unsubstituted oxyalkylenearyl, or mixtures thereof;
p) substituted alkyleneoxyaryl, unsubstituted alkyleneoxyaryl, or mixtures thereof;
q) $C_1$–$C_{22}$ thioalkyl, $C_3$–$C_{22}$ branched thioalkyl, or mixtures thereof;
r) an alkyleneamino unit of the formula

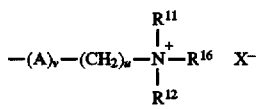

wherein $R^{11}$ and $R^{12}$ is $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof; $R^{16}$ is:
  i) hydrogen;
  ii) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;
  A is nitrogen or oxygen; X is a water soluble anion, v is 0 or 1, u is from 1 to 22;

s) an amino unit of the formula

wherein $R^{11}$ and $R^{12}$ is $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

t) an alkylethyleneoxy unit of the formula

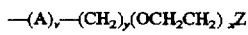
—(A)$_v$—(CH$_2$)$_x$(OCH$_2$CH$_2$)$_y$Z wherein Z is:
i) hydrogen;
ii) hydroxyl;
iii) —CO$_2$H;
iv) —SO$_3$-M$^+$;
v) —OSO$_3$-M$^+$;
vi) C$_1$–C$_6$ alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;

A is nitrogen or oxygen, M is a water soluble cation, v is 0 or 1, x is from 0 to 100, y is from 0 to 12;

u) carboxylate of the formula

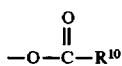
—O—C(=O)—R$^{10}$ wherein R$^{10}$ is:
i) C$_1$–C$_{22}$ alkyl, C$_3$–C$_{22}$ branched alkyl, C$_3$–C$_{22}$ alkenyl, C$_3$–C$_{22}$ branched alkenyl, or mixtures thereof;
ii) halogen substituted C$_1$–C$_{22}$ alkyl, C$_3$–C$_{22}$ branched alkyl, C$_3$–C$_{22}$ alkenyl, C$_3$–C$_{22}$ branched alkenyl, or mixtures thereof;
iii) poly-hydroxyl substituted C$_3$–C$_{22}$ alkyl;
iv) C$_3$–C$_{22}$ glycol;
v) C$_1$–C$_{22}$ alkoxy;
vi) C$_3$–C$_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;
x) substituted oxyalkylenearyl, unsubstituted oxyalkylenearyl, or mixtures thereof;
xi) substituted alkyleneoxyaryl, unsubstituted alkyleneoxyaryl, or mixtures thereof;

v) substituted siloxy of the formula

—OSiR$^7$R$^8$R$^9$ wherein each R$^7$, R$^8$, and R$^9$ is independently:
i) C$_1$–C$_{22}$ alkyl, C$_3$–C$_{22}$ branched alkyl, C$_3$–C$_{22}$ alkenyl, C$_3$–C$_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula

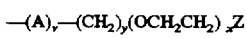
—(A)$_v$—(CH$_2$)$_x$(OCH$_2$CH$_2$)$_y$Z wherein Z comprises:
a) hydrogen;
b) C$_1$–C$_{30}$ alkyl,
c) hydroxyl;
d) —CO$_2$H;
e) —SO$_3$-M$^+$;
f) —OSO$_3$-M$^+$;
g) C$_1$–C$_6$ alkoxy;
h) substituted aryl, unsubstituted aryl, or mixtures thereof;
i) substituted aryloxy, unsubstituted aryloxy, or mixtures thereof;
j) alkyleneamino; and mixtures thereof;

A is nitrogen or oxygen, M is a water soluble cation, v is 0 or 1, x is from 0 to 100, y is from 0 to 12; mixtures thereof.

35. A silicon phthalocyanine or silicon naphtlalocyanine photodisinfecting composition comprising:
a) a silicon(IV) phthalocyanine of the formula

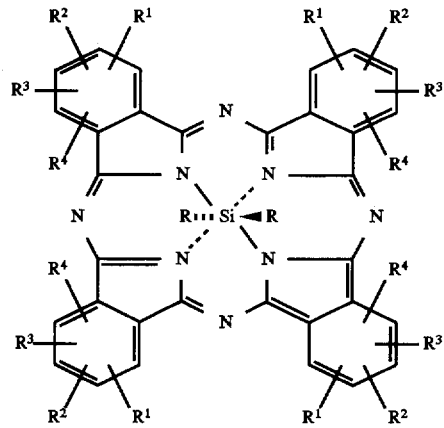

or a silicon(IV) naphthalocyanine of the formula

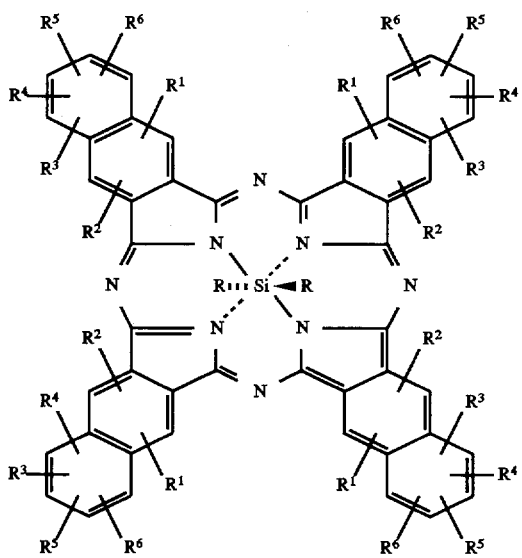

wherein R$^1$, R$^2$, R$^3$, R$^4$, R$^5$, and R$^6$ units are moieties that provide a positive red shift value of at least 1 when said moieties are substituted for hydrogen; wherein the R units are axial units, said R units independently selected from the group consisting of:
a) hydrogen;
b) halogen;
c) hydroxyl;

d) cyano;

e) nitrilo;

f) oximino;

g) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

h) halogen substituted $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

i) polyhydroxyl substituted $C_3$–$C_{22}$ alkyl;

j) $C_1$–$C_{22}$ alkoxy;

k) branched alkoxy having the formula

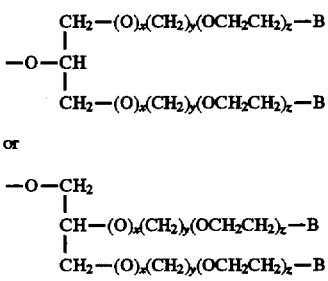

wherein B is hydrogen, hydroxyl, $C_1$–$C_{30}$ alkyl, $C_1$–$C_{30}$ alkoxy, —$CO_2H$, —$CH_2CO_2H$, —$SO_3$-$M^+$, —$OSO_3$-$M^+$, —$PO_3^{2-}M$, —$OPO_3^{2-}M$, or mixtures thereof; M is a water soluble cation; x is 0 or 1, each y independently has the value from 0 to 6, each z independently has the value from 0 to 100;

l) substituted aryl, unsubstituted aryl, or mixtures thereof;

m) substituted alkylenearyl, unsubstituted alkylenearyl, or mixtures thereof;

n) substituted aryloxy, unsubstituted aryloxy, or mixtures thereof;

o) substituted oxyalkylenearyl, unsubstituted oxyalkylenearyl, or mixtures thereof;

p) substituted alkyleneoxyaryl, unsubstituted alkyleneoxyaryl, or mixtures thereof;

q) $C_1$–$C_{22}$ thioalkyl, $C_3$–$C_{22}$ branched thioalkyl, or mixtures thereof;

r) an alkyleneamino unit of the formula

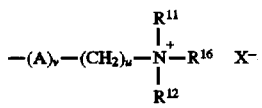

wherein $R^{11}$ and $R^{12}$ is $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof; $R^{16}$ is:

i) hydrogen;

ii) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

A is nitrogen or oxygen; X is a water soluble anion, v is 0 or 1, u is from 1 to 22;

s) an amino unit of the formula

—$NR^{11}R^{12}$ wherein $R^{11}$ and $R^{12}$ is $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

t) an alkylethyleneoxy unit of the formula

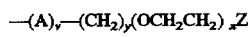

wherein Z is:

i) hydrogen;

ii) hydroxyl;

iii) —$CO_2H$;

iv) —$SO_3$-$M^+$;

v) —$OSO_3$-$M^+$;

vi) $C_1$–$C_6$ alkoxy;

vii) substituted aryl, unsubstituted aryl, or mixtures thereof;

viii) substituted alkylenearyl, unsubstituted alkylenearyl, or mixtures thereof;

ix) substituted aryloxy, unsubstituted aryloxy, or mixtures thereof;

A is nitrogen or oxygen, M is a water soluble cation, v is 0 or 1, x is from 0 to 100, y is from 0 to 12;

u) carboxylate of the formula

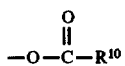

wherein $R^{10}$ is:

i) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

ii) halogen substituted $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

iii) poly-hydroxyl substituted $C_3$–$C_{22}$ alkyl;

iv) $C_3$–$C_{22}$ glycol;

v) $C_1$–$C_{22}$ alkoxy;

vi) $C_4$–$C_{22}$ branched alkoxy;

vii) substituted aryl, unsubstituted aryl, or mixtures thereof;

viii) substituted alkylenearyl, unsubstituted alkylenearyl, or mixtures thereof;

ix) substituted aryloxy, unsubstituted aryloxy, or mixtures thereof;

x) substituted oxyalkylenearyl, unsubstituted oxyalkylenearyl, or mixtures thereof;

xi) substituted alkyleneoxyaryl, unsubstituted alkyleneoxyaryl, or mixtures thereof;

v) substituted siloxy of the formula

—$OSiR^7R^8R^9$ wherein each $R^7$, $R^8$, and $R^9$ is independently:

i) $C_1$–$C_{22}$ alkyl, $C_3$–$C_{22}$ branched alkyl, $C_3$–$C_{22}$ alkenyl, $C_3$–$C_{22}$ branched alkenyl, or mixtures thereof;

ii) substituted aryl, unsubstituted aryl, or mixtures thereof;

iii) substituted aryloxy, unsubstituted aryloxy, or mixtures thereof;

iv) an alkylethyleneoxy unit of the formula

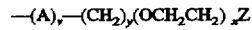

wherein Z comprises:

a) hydrogen;

b) $C_1$–$C_{30}$ alkyl, c) hydroxyl;
d) —CO$_2$H;
e) —SO$_3$-M$^+$;
f) —OSO$_3$-M$^+$;
g) C$_1$-C$_6$ alkoxy;
h) substituted aryl, unsubstituted aryl, or mixtures thereof;
i) substituted aryloxy, unsubstituted aryloxy, or mixtures thereof;
j) alkyleneamino; and mixtures thereof;

A is nitrogen or oxygen, M is a water soluble cation, v is 0 or 1, x is from 0 to 100, y is from 0 to 12; and mixtures thereof; and b) the balance adjunct ingredients.

36. A silicon phthalocyanine or silicon naphthalocyanine photodisinfecting composition comprising:

a) a silicon(IV) phthalocyanine of the formula

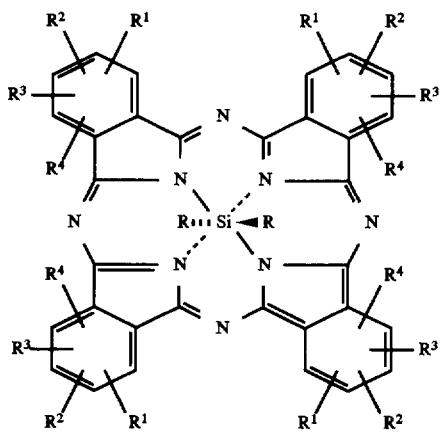

or a silicon(IV) naphthalocyanine of the formula

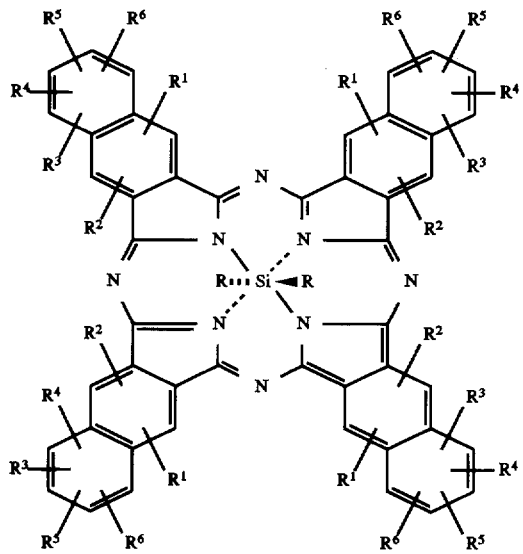

wherein R$^1$, R$^2$, R$^3$, R$^4$, R$^5$, and R$^6$ units are moieties that provide a positive $\Delta_{triplet}$ yield when said moiety replaces hydrogen; wherein the R units are axial units, said R units independently selected from the group consisting of:

a) hydrogen;
b) halogen;
c) hydroxyl;
d) cyano;
e) nitrilo;
f) oximino;
g) C$_1$-C$_{22}$ alkyl, C$_3$-C$_{22}$ branched alkyl, C$_3$-C$_{22}$ alkenyl, C$_3$-C$_{22}$ branched alkenyl, or mixtures thereof;
h) halogen substituted C$_1$-C$_{22}$ alkyl, C$_3$-C$_{22}$ branched alkyl, C$_3$-C$_{22}$ alkenyl, C$_3$-C$_{22}$ branched alkenyl, or mixtures thereof;
i) polyhydroxyl substituted C$_3$-C$_{22}$ alkyl;
j) C$_1$-C$_{22}$ alkoxy;
k) branched alkoxy having the formula

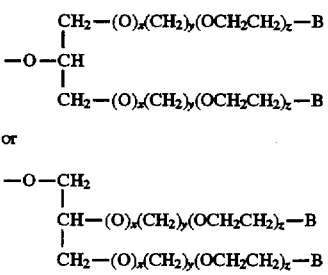

wherein B is hydrogen, hydroxyl, C$_1$-C$_{30}$ alkyl, C$_1$-C$_{30}$ alkoxy, —CO$_2$H, —CH$_2$CO$_2$H, —SO$_3$-M$^+$, —OSO$_3$-M$^+$, —PO$_3^{2-}$M, —OPO$_3^{2-}$M, or mixtures thereof; M is a water soluble cation; x is 0 or 1, each y independently has the value from 0 to 6, each z independently has the value from 0 to 100;

l) substituted aryl, unsubstituted aryl, or mixtures thereof;
m) substituted alkylenearyl, unsubstituted alkylenearyl, or mixtures thereof;
n) substituted aryloxy, unsubstituted aryloxy, or mixtures thereof;
o) substituted oxyalkylenearyl, unsubstituted oxyalkylenearyl, or mixtures thereof;
p) substituted alkyleneoxyaryl, unsubstituted alkyleneoxyaryl, or mixtures thereof;
q) C$_1$-C$_{22}$ thioalkyl, C$_3$-C$_{22}$ branched thioalkyl, or mixtures thereof;
r) an alkyleneamino unit of the formula

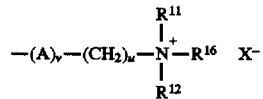

wherein R$^{11}$ and R$^{12}$ is C$_1$-C$_{22}$ alkyl, C$_3$-C$_{22}$ branched alkyl, C$_3$-C$_{22}$ alkenyl, C$_3$-C$_{22}$ branched alkenyl, or mixtures thereof; R$^{16}$ is:

i) hydrogen;
ii) C$_1$-C$_{22}$ alkyl, C$_3$-C$_{22}$ branched alkyl, C$_3$-C$_{22}$ alkenyl, C$_3$-C$_{22}$ branched alkenyl, or mixtures thereof;

A is nitrogen or oxygen; X is a water soluble anion, v is 0 or 1, u is from 1 to 22;

s) an amino unit of the formula

wherein R$^{11}$ and R$^{12}$ is C$_1$-C$_{22}$ alkyl, C$_3$-C$_{22}$ branched alkyl, C$_3$-C$_{22}$ alkenyl, C$_3$-C$_{22}$ branched alkenyl, or mixtures thereof;

t) an alkylethyleneoxy unit of the formula $$-(A)_v-(CH_2)_x(OCH_2CH_2)_y Z$$

wherein Z is:
- i) hydrogen;
- ii) hydroxyl;
- iii) —$CO_2H$;
- iv) —$SO_3^-M^+$;
- v) —$OSO_3^-M^+$;
- vi) $C_1-C_6$ alkoxy;
- vii) substituted aryl, unsubstituted aryl, or mixtures thereof;
- viii) substituted alkylenearyl, unsubstituted alkylenearyl, or mixtures thereof;
- ix) substituted aryloxy, unsubstituted aryloxy, or mixtures thereof;

A is nitrogen or oxygen, M is a water soluble cation, v is 0 or 1, x is from 0 to 100, y is from 0 to 12;

u) carboxylate of the formula $$-O-\overset{O}{\underset{\|}{C}}-R^{10}$$

wherein $R^{10}$ is:
- i) $C_1-C_{22}$ alkyl, $C_3-C_{22}$ branched alkyl, $C_3-C_{22}$ alkenyl, $C_3-C_{22}$ branched alkenyl, or mixtures thereof;
- ii) halogen substituted $C_1-C_{22}$ alkyl, $C_3-C_{22}$ branched alkyl, $C_3-C_{22}$ alkenyl, $C_3-C_{22}$ branched alkenyl, or mixtures thereof;
- iii) poly-hydroxyl substituted $C_3-C_{22}$ alkyl;
- iv) $C_3-C_{22}$ glycol;
- v) $C_1-C_{22}$ alkoxy;
- vi) $C_4-C_{22}$ branched alkoxy;
- vii) substituted aryl, unsubstituted aryl, or mixtures thereof;
- viii) substituted alkylenearyl, unsubstituted alkylenearyl, or mixtures thereof;
- ix) substituted aryloxy, unsubstituted aryloxy, or mixtures thereof;
- x) substituted oxyalkylenearyl, unsubstituted oxyalkylenearyl, or mixtures thereof;
- xi) substituted alkyleneoxyaryl, unsubstituted alkyleneoxyaryl, or mixtures thereof;

v) substituted siloxy of the formula $$-OSiR^7R^8R^9$$

wherein each $R^7$, $R^8$, and $R^9$ is independently:
- i) $C_1-C_{22}$ alkyl, $C_3-C_{22}$ branched alkyl, $C_3-C_{22}$ alkenyl, $C_3-C_{22}$ branched alkenyl, or mixtures thereof;
- ii) substituted aryl, unsubstituted aryl, or mixtures thereof;
- iii) substituted aryloxy, unsubstituted aryloxy, or mixtures thereof;
- iv) an alkylethyleneoxy unit of the formula $$-(A)_v-(CH_2)_x(OCH_2CH_2)_y Z$$

wherein Z comprises:
- a) hydrogen;
- b) $C_1-C_{30}$ alkyl,
- c) hydroxyl;
- d) —$CO_2H$;
- e) —$SO_3^-M^+$;
- f) —$OSO_3^-M^+$;
- g) $C_1-C_6$ alkoxy;
- h) substituted aryl, unsubstituted aryl, or mixtures thereof;
- i) substituted aryloxy, unsubstituted aryloxy, or mixtures thereof;
- j) alkyleneamino; and mixtures thereof;

A is nitrogen or oxygen, M is a water soluble cation, v is 0 or 1, x is from 0 to 100, y is from 0 to 12;

and mixtures thereof; and b) the balance adjunct ingredients.

* * * * *